United States Patent [19]
Barlozzari et al.

[11] Patent Number: 6,015,790
[45] Date of Patent: Jan. 18, 2000

[54] METHODS AND COMPOSITIONS FOR TREATING RHEUMATOID ARTHRITIS

[75] Inventors: Teresa Barlozzari, Wellesley; Subhashis Banerjee, Shrewsbury; Andreas Haupt, Northborough, all of Mass.

[73] Assignee: BASF Aktiengesellschaft, Ludwigshafen, Germany

[21] Appl. No.: 08/944,479

[22] Filed: Oct. 6, 1997

[51] Int. Cl.[7] .................................................. A61K 38/00
[52] U.S. Cl. .............................. 514/17; 514/18
[58] Field of Search .......................... 514/17, 18

[56] References Cited

U.S. PATENT DOCUMENTS

| | | | |
|---|---|---|---|
| 4,816,444 | 3/1989 | Pettit et al. ................................ | 514/17 |
| 5,502,032 | 3/1996 | Haupt et al. ................................ | 514/17 |
| 5,504,191 | 4/1996 | Pettit et al. ................................ | 530/330 |
| 5,530,097 | 6/1996 | Pettit et al. ................................ | 530/330 |
| 5,583,153 | 12/1996 | Brahn ........................................ | 514/449 |

FOREIGN PATENT DOCUMENTS

| | | |
|---|---|---|
| 0 398 558 A1 | 11/1990 | European Pat. Off. . |
| 0 598 129 A1 | 5/1994 | European Pat. Off. . |
| WO 96/40751 A1 | 12/1996 | WIPO . |
| WO 96/40752 A1 | 12/1996 | WIPO . |

OTHER PUBLICATIONS

Massarotti, E.M., "Medical Aspects of Rheumatoid Arthritis: Diagnosis and Treatment," *Oncology,* 12(3):463–475(1996).

Harris, E.D., "Rheumatoid Arthritis: Pathophysiology and Implications for Therapy," *N. Engl. J. Med.,* 332(18):1277–1289(1990).

Beckwith, M., et al., "Growth Inhibition of Human Lymphoma Cell Lines by the Marine Products, Dolastatins 10 and 15," *J. Natl. Cancer Inst.,* 85(6):483–488(1993).

Galéotti, N., et al., "Formation of Oxazolines and Thiazolines in Peptides by the Mitsunobu Reaction," *Tetrahedron Letters,* 33(20):2807–2810(1992).

Wipf, P., and Miller, C.P., "A Short, Stereospecific Synthesis of Dihydrooxazoles from Serine and Threonine Derivatives," *Tetrahedron Letters,* 33(7):907–910(1992).

Tully, W.R., et al., "2–(Oxadiazolyl)– and 2–(Thiazolyl)imidazo[1,2–a]pyrimidines as Agonists and Inverse Agonists at Benzodiazepine Receptors," *J. Med. Chem.,* 34:2060–2067(1991).

Freidinger, R.M., et al., "Protected Lactam–Bridged Dipeptides for Use as Conformational Constraints in Peptides," *J. Org. Chem.,* 47:104–109(1982).

Pettit, G.R., et al., "Isolation and Structure of the Cytostatic Linear Depsipeptide Dolastatin $15^{1a}$," *J. Org. Chem.,* 54:6005–6006(1989).

Bai, R., et al., "Dolastatin 15, a potent antimitotic depsipeptide derived from *Dolabella auricularia.* Interaction with tubulin and effects on cellular microtubules," *Biochem. Pharmacol.* 43(12):2637–2645(1992). (Abstract 117: 103735g from *1–Pharmacology,* p. 41, 1992).

Pettit, G.R., et al., "Antineoplastic Agents. 220. Synthesis of Natural (–)–Dolastatin $15^1$," *J. Am. Chem. Soc.,* 113:6693–6695(1991).

Banerjee, S., et al., "Influence of Complement C5 and $V_\beta$ T Cell Receptor Mutations on Susceptibility to Collagen–Induced Arthritis in Mice[1]," *J. Immunol,* 142(7):2237–2243(1989).

*Primary Examiner*—Theodore J. Criares
*Attorney, Agent, or Firm*—Hamilton, Brooks, Smith & Reynolds, P.C.

[57] ABSTRACT

The present invention provides compositions and methods for the treatment of rheumatoid arthritis in a subject wherein one or more compounds of Formula I as defined herein alone or in combination with one or more other antiarthritic drugs provide suppression of rheumatoid arthritis.

11 Claims, 6 Drawing Sheets

(i)

(ii)

(iii)

(iv)

(v)

(vi)

(vii)

(viii)

(ix)

(x)

(xi)

(xii)

(xiii)

(xiv)

(xv)

(xvi)

(xvii)

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
       (A) LENGTH: 5 amino acids
       (B) TYPE: amino acid
       (C) STRANDEDNESS:
       (D) TOPOLOGY: linear (ii) MOLECULE TYPE: peptide (xi) SEQUENCE DESCRIPTION: SEQ ID NO:1:

Xaa Val Xaa Pro Xaa
1               5

(2) INFORMATION FOR SEQ ID NO:2:

(i) SEQUENCE CHARACTERISTICS:
       (A) LENGTH: 5 amino acids
       (B) TYPE: amino acid
       (C) STRANDEDNESS:
       (D) TOPOLOGY: linear (ii) MOLECULE TYPE: peptide (xi) SEQUENCE DESCRIPTION: SEQ ID NO:2:

Xaa Xaa Xaa Pro Xaa
1               5

(2) INFORMATION FOR SEQ ID NO:3:

(i) SEQUENCE CHARACTERISTICS:
       (A) LENGTH: 6 amino acids
       (B) TYPE: amino acid
       (C) STRANDEDNESS:
       (D) TOPOLOGY: linear (ii) MOLECULE TYPE: peptide (xi) SEQUENCE DESCRIPTION: SEQ ID NO:3:

Xaa Val Xaa Pro Pro Xaa
1               5

(2) INFORMATION FOR SEQ ID NO:4:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

Xaa Xaa Xaa Pro Xaa
1               5

(2) INFORMATION FOR SEQ ID NO:5:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

Xaa Ile Xaa Pro Xaa
1               5

(2) INFORMATION FOR SEQ ID NO:6:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

Xaa Val Xaa Pro Pro Val Phe
1               5

(2) INFORMATION FOR SEQ ID NO:7:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:7:

Xaa Val Xaa Pro Xaa Val Phe
1               5

(2) INFORMATION FOR SEQ ID NO:8:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

Xaa Ile Xaa Pro Pro Val Phe
1               5

```
(2) INFORMATION FOR SEQ ID NO:9:

(i) SEQUENCE CHARACTERISTICS:
         (A) LENGTH: 7 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:9:

Xaa Leu Xaa Pro Pro Val Phe
1               5

(2) INFORMATION FOR SEQ ID NO:10:

(i) SEQUENCE CHARACTERISTICS:
         (A) LENGTH: 7 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:10:

Xaa Val Xaa Pro Pro Phe Phe
1               5

(2) INFORMATION FOR SEQ ID NO:11:

(i) SEQUENCE CHARACTERISTICS:
         (A) LENGTH: 6 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:11:

Xaa Val Xaa Pro Pro Val
1               5

(2) INFORMATION FOR SEQ ID NO:12:

(i) SEQUENCE CHARACTERISTICS:
         (A) LENGTH: 5 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:12:

Xaa Val Xaa Pro Pro
1               5

(2) INFORMATION FOR SEQ ID NO:13:

(i) SEQUENCE CHARACTERISTICS:
         (A) LENGTH: 4 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:13:

Xaa Val Xaa Xaa
1
```

(2) INFORMATION FOR SEQ ID NO:14:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:14:

Xaa Xaa Xaa Pro Pro
1            5

(2) INFORMATION FOR SEQ ID NO:15:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:15:

Xaa Val Xaa Pro Pro Xaa Phe
1            5

(2) INFORMATION FOR SEQ ID NO:16:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:16:

Xaa Val Xaa Pro Pro Leu Phe
1            5

(2) INFORMATION FOR SEQ ID NO:17:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:17:

Xaa Val Xaa Pro Pro Ile Phe
1            5

METHODS AND COMPOSITIONS FOR TREATING RHEUMATOID ARTHRITIS

BACKGROUND OF THE INVENTION

Rheumatoid arthritis is generally considered an autoimmune disease that is thought to be associated with activity of autoreactive T cells (See, e.g., Harris, E. D., Jr., *The New England Journal of Medicine*, 322: 1277–1289 (1990)). Despite advances in treatment, rheumatoid arthritis remains a serious health problem. Although rarely fatal, arthritis is a major cause of morbidity, loss of time from work, lost productivity and decrease in quality of life. Rheumatoid arthritis causes severe pain and loss of joint mobility and can make accomplishing even simple tasks difficult.

Current treatment methods and regimes for rheumatoid arthritis include administration of non-steroidal anti-inflammatory drugs such as acetylsalicylic acid (aspirin), ibuprofen, naproxen and other such agents, gold compounds, penicillamine, methotrexate, cytotoxic agents (e.g., azothrioprine), 4-aminoquinoline agents, and immunomodulators. However, improved treatments of rheumatoid arthritis, which can suppress or ameliorate symptoms such as inflammation, swelling, abnormal neovascularization, bone erosion, or cartilage erosion are needed. Preferably, such an improved method of treatment should be able to be combined with other treatment methods, should work rapidly to cause regression or stabilization of symptoms, and should be well tolerated. Preferably, such a treatment regime should also be useful in prophylaxis in susceptible individuals.

SUMMARY OF THE INVENTION

This invention relates to Dolastatin-15 derivatives, their preparation and use in the treatment of rheumatoid arthritis, in a mammal, for example a human. The Dolastatin-15 derivatives of the present invention are compounds of Formula I:

$$R^1R^2N—CHX—CO—A—B—D—(E)_s—(F)_t—(G)_u—K \quad (I)$$

Formula I is discussed in detail below. Some examples of compounds of Formula I are specifically presented herein. For example, compounds of Formula I can be those in which $R^1$ and $R^2$ are each methyl or ethyl; X is isopropyl, sec-butyl or tert-butyl; s is 1; t and u are each 0; A is valyl, isoleucyl or 2-tert-butylglycyl; B is N-methylvalyl, 1-isoleucyl or 2-tert-butylglycyl; D is thiazolidinyl-carbonyl, 3,4-dehydroprolyl or prolyl; E is prolyl, thiazolidinyl-4-carbonyl, homoprolyl, hydroxyprolyl or 3,4-dehydroprolyl; and K is a substituted amino moiety having the formula $R^5—N—R^6$, wherein $R^5$ is hydrogen or $C_1–C_4$-alkoxy and $R^6$ is a monovalent radical such as (1)- or (2)-adamantyl; $(CH_2)v$-phenyl with v=1; α,α-dimethylbenzyl; a $C_1–C_{12}$ linear or branched hydroxyalkyl group, such as —C(CH$_3$)$_2$—CH$_2$—CH$_2$—OH, also referred to as 3-hydroxy-1,1-dimethylpropyl; a $C_3–Cl_{10}$ cycloalkyl group, such as bicyclo [3.3.0]octa-1-yl, 1-methylcyclopentyl or 1-methylcyclohexyl; or a $C_1–C_{12}$ linear or branched alkyl group, such as —C(CH$_3$)$_3$, also referred to as tert-butyl;

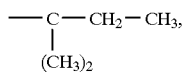

also referred to as 1,1-dimethylpropyl;

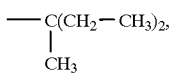

also referred to as 1-methyl-1-ethylpropyl;

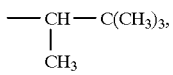

also referred to as (S)- or (R)-1-methyl-2,2-dimethyl-propyl;

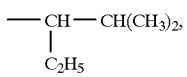

also referred to as (S)- or (R)-1-ethyl-2-methylpropyl;

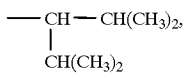

also referred to as 1-isopropyl-2-methyl-propyl; or
—C(CH$_3$)$_2$—CH(CH$_3$)$_2$, also referred to as 1,1-dimethyl-2-methylpropyl;
—CH(CH$_3$)$_2$, also referred to as isopropyl;
—CH(CH$_3$) CH$_2$CH$_3$, sec-butyl [(S) or (R)]; or
—CH(CH$_3$) CH(CH$_3$)$_2$, also referred to as 1,2-dimethylpropyl.

This invention also relates to methods for the treatment of rheumatoid arthritis, in a mammal, for example a human, in which one or more of the Dolastatin-15 derivatives described herein are used. In the method of the present invention, one or more of the Dolastatin-15 derivatives are administered, alone or in a pharmacologically acceptable carrier, in a therapeutically effective amount to treat rheumatoid arthritis in a mammal having or susceptible to rheumatoid arthritis.

In another aspect of the invention one or more Dolastatin-15 derivatives are administered in combination with one or more other antiarthritic drugs to a mammal having or susceptible to rheumatoid arthritis.

In a specific embodiment, two or more Dolastatin-15 derivatives are administered alone or in combination with one or more other antiarthritic drugs to a mammal having or susceptible to rheumatoid arthritis. Administration of two or more Dolastatin-15 derivatives or administration of Dolastatin-15 derivative(s) in combination with one or more other antiarthritic drugs enhances treatment of rheumatoid arthritis. For example, a combination provides a greater suppression or fewer side effects, and/or can make it possible to administer a lower dose of the known antiarthritic drug to produce the same effect produced with a higher dose. The other antiarthritic drug can be, but is not limited to, one or more of the following: (1) a nonsteroidal anti-inflammatory agent such acetylsalicylic (aspirin), ibuprofen, or naproxen; (2) an organic gold derivative such a gold sodium thiomalate, aurothioglucose, or auranofin; (3) D-pencillamine; (4) a 4-aminoquinoline agent such as hydroxychloroquine; (5) azathioprine; (6) methotrexate; (7) cyclosporin; (8) an angiogenesis inhibitor such as AGM-1470 (Ingber, et al., *Nature* 348, (1990) 555); (9) monoclonal antibodies to T cells; (10) monoclonal antibodies to adhesion molecules; (11) monoclonal antibodies to cytokines and growth factors; (12) Tumor Necrosis Factor Receptor (TNFR)-IgG; (13) IL-1 receptor antagonists; and (14) ICE inhibitors.

Also the subject of this invention are pharmaceutical compositions which comprise one or more Dolastatin-15 derivatives of Formula I either alone or in combination with one or more other antiarthritic drugs. The pharmaceutical composition can optionally include a pharmaceutically acceptable carrier, diluent or a compound which aids in processing, for example, binders, fillers and preservatives.

DETAILED DESCRIPTION OF THE INVENTION

Figure 1A:
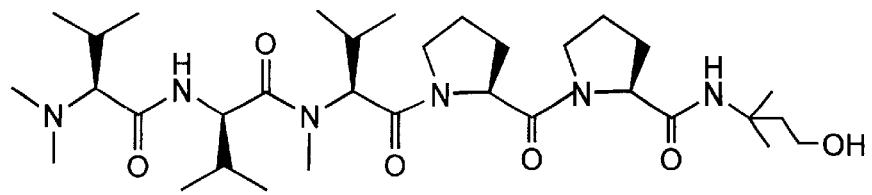
FIGS. 1A–1D depict compounds i-xvii, as examples of Dolastatin-15 derivatives having the structure of Formula I.
Figure 1A:
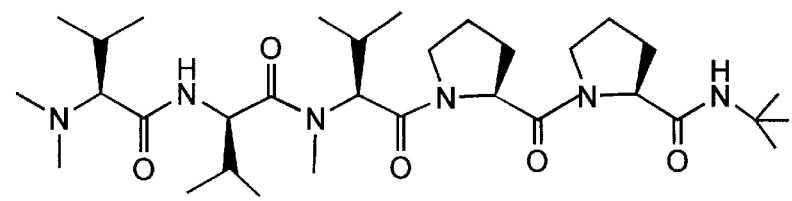
Figure 1A:
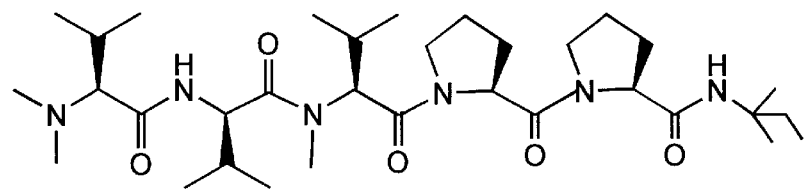
Figure 1A:
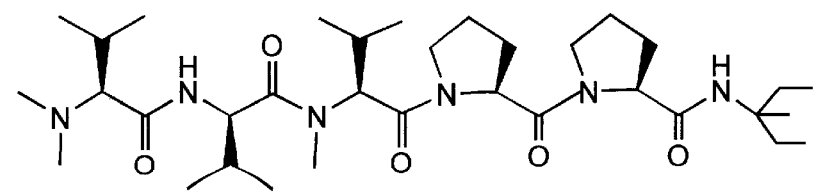
Figure 1B:
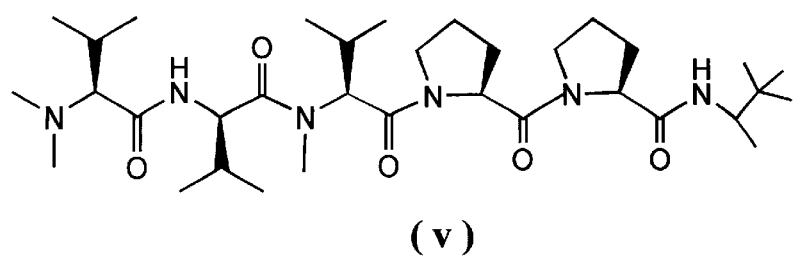
Figure 1B:
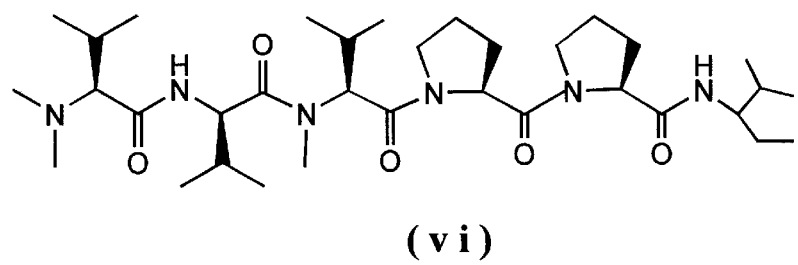
Figure 1B:
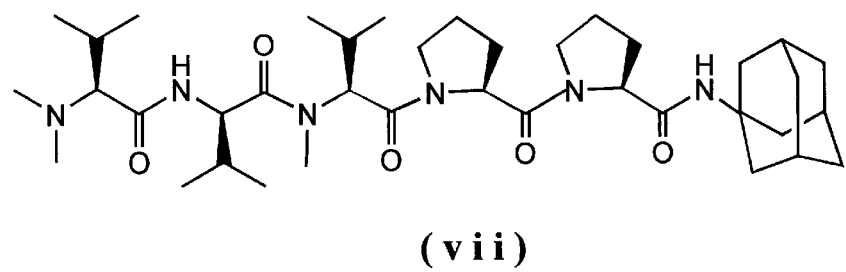
Figure 1B:
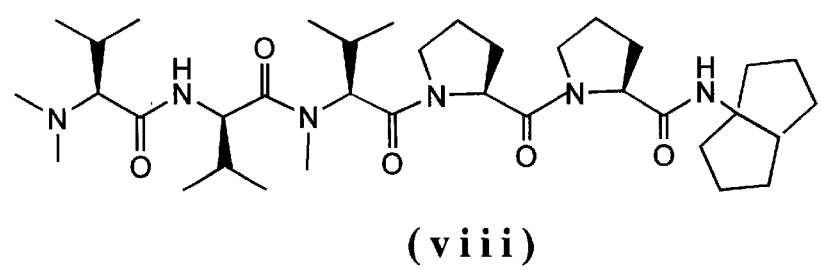
Figure 1C:
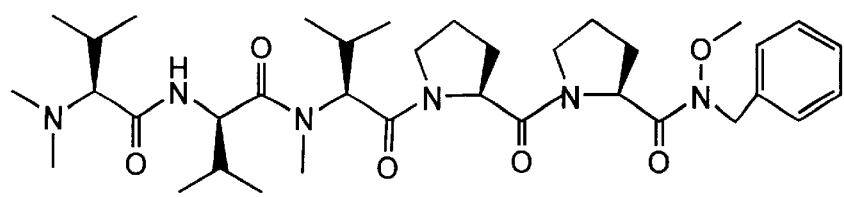
Figure 1C:
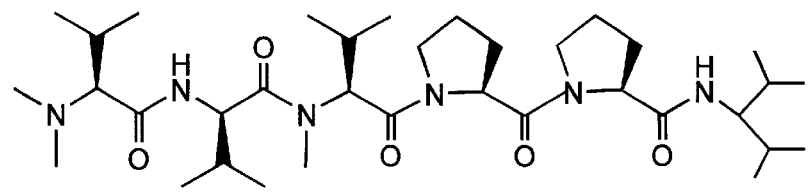
Figure 1C:
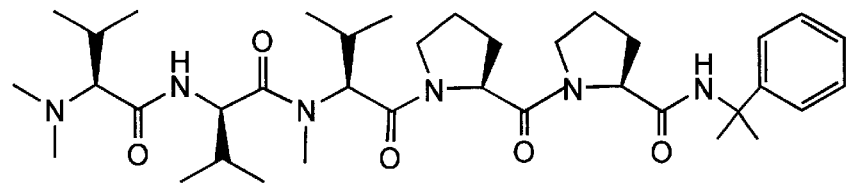
Figure 1C:
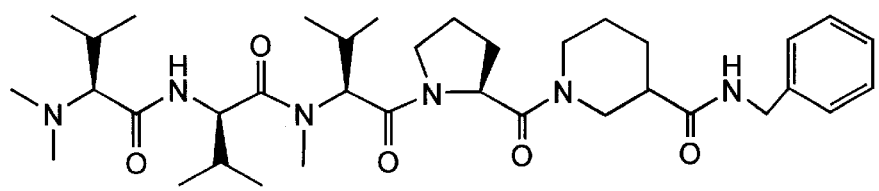
Figure 1D:
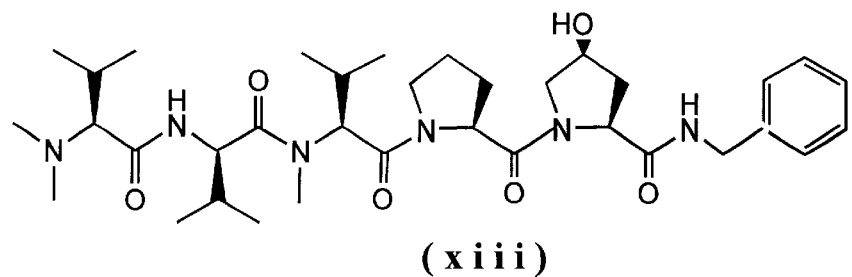
Figure 1D:
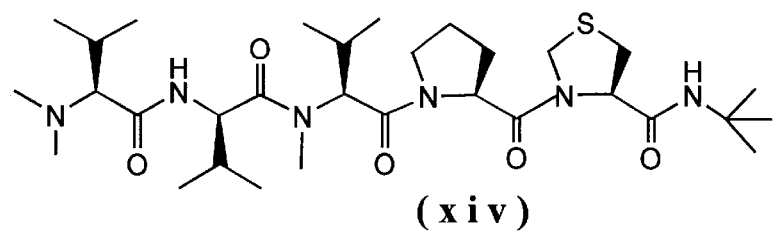
Figure 1D:
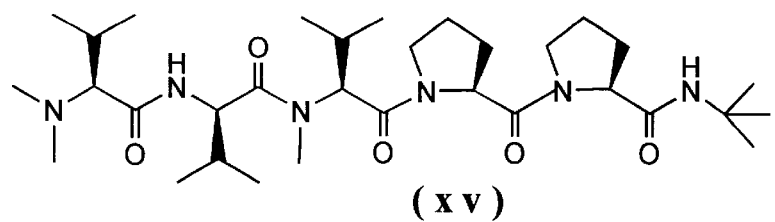
Figure 1D:
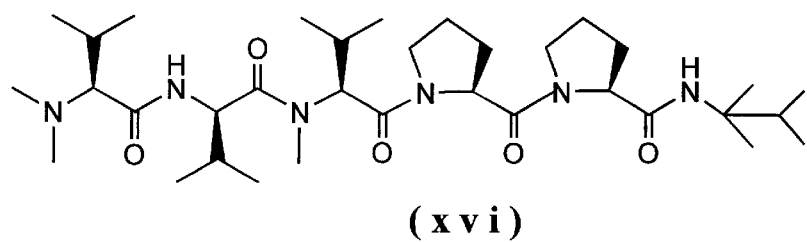
Figure 1D:
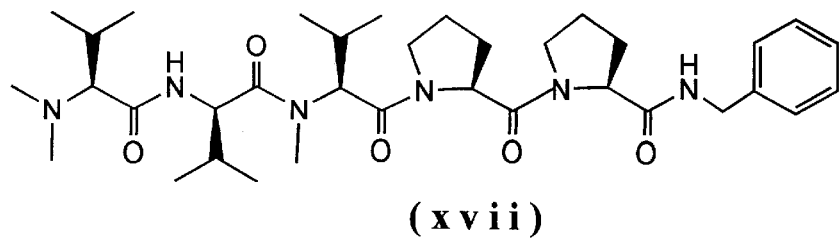

The present invention relates to Dolastatin-15 derivatives useful in the treatment of rheumatoid arthritis in a mammal. The Dolastatin-15 derivatives of the invention are compounds having the structure shown in Formula I, as further described below. The compound is administered in a therapeutically effective amount. As used herein the term "therapeutically effective amount" refers to an amount sufficient to elicit the desired biological response. In this invention, the desired biological response of the treatment is suppression of rheumatoid arthritis. As used herein "suppression" includes any or all of the following: (1) amelioration of existing symptoms; (2) prevention or slowing of the progression of symptoms; (3) prevention or delay of the inception or occurrence of the disease in a susceptible subject, i.e., prophylaxis. Symptoms typically associated with rheumatoid arthritis, include but are not limited to, inflammation, swelling, abnormal neovascularization, bone erosion and cartilage erosion. One or more of these symptoms are suppressed when a therapeutically effective amount of a Dolastatin-15 derivative compound of Formula I is administered.

Compounds of Formula I

A number of short peptides with significant activity as inhibitors of cell growth have been isolated from the Indian Ocean sea hare *Dolabella auricularia* (Bai, et al., *Biochem. Pharmacology*, 40: 1859–1864 (1990); Beckwith et al., *J. Natl. Cancer Inst.*, 85: 483–488 (1993) and references cited therein). These include Dolastatins 1–10 (U.S. Pat. No. 4,816,444, issued to Pettit et al.) and Dolastatin-15 (European Patent Application No. 398558). Dolastatin-15, for example, markedly inhibits the growth of the National Cancer Institute's P388 lymphocytic leukemia cell line, a strong predictor of efficacy against various types of human malignancies. This compound, however, is present only in trace quantities in the sea hare and is difficult to isolate, expensive to synthesize and suffers from poor aqueous solubility.

The compounds of Formula I are derivatives of Dolastatin-15. It has been determined that, surprisingly, the compounds of Formula I are useful in a method for the treatment of rheumatoid arthritis. Dolastatin-15 derivatives of Formula I, which are employed in the method of the present invention, can be synthesized, as described herein and in related copending application U.S. Ser. No. 08/472, 453, filed Jun. 7, 1995, the teachings of which are incorporated herein in their entirety.

The Dolastatin-15 derivatives of Formula I generally comprise L-amino acids, but they can also contain one or more D-amino acids, as described in related copending application U.S. Ser. No. 08/472,453 filed on Jun. 7, 1995. The compounds of Formula I can also be present as salts with physiologically-compatible acids, such as, but not limited to, hydrochloric acid, citric acid, tartaric acid, lactic acid, phosphoric acid, methanesulfonic acid, acetic acid, formic acid, maleic acid, fumaric acid, malic acid, succinic acid, malonic acid, sulfuric acid, L-glutamic acid, L-aspartic acid, pyruvic acid, mucic acid, benzoic acid, glucuronic acid, oxalic acid, ascorbic acid and acetylglycine.

For purposes of the present invention, the term "monovalent radical" is intended to mean an electrically neutral molecular fragment capable of forming one covalent bond with a second neutral molecular fragment. Monovalent radicals include the hydrogen atom, alkyl groups (e.g. methyl, ethyl, propyl and tert-butyl groups), cycloalkyl groups, hydroxy alkyl groups, adamantyl groups, halogen atoms (e.g. fluorine, chlorine and bromine atoms), aryl groups (e.g. phenyl, benzyl and naphthyl groups) and alkoxy groups (e.g. methoxy and ethoxy groups). Two monovalent radicals on adjacent sigma-bonded atoms can also form a pi bond between the adjacent atoms. Two monovalent radicals may also be linked together, for example, by a polymethylene unit to form a cyclic structure. For example, the unit —N(R)R', wherein R and R' are monovalent radicals, can, together with the nitrogen atom, form a heterocyclic ring. In addition, two monovalent radicals bonded to the same atom can also form a divalent radical, such as an alkylidene group, for example, a propylidene group, or an oxygen atom.

More specifically, for the compounds of Formula I:

$R^1$ is alkyl, such as $C_1$–$C_3$; cycloalkyl, such as cyclopropyl; alkylsulfonyl, such as $C_1$–$C_3$; fluoroalkyl, such as fluoroethyl, difluoroethyl, fluoroisopropyl; aminosulfonyl which may be substituted by alkyl, such as methyl;

$R^2$ is hydrogen; alkyl, such as $C_1$–$C_3$; fluoroalkyl, such as fluoroethyl, difluoroethyl, fluoroisopropyl; cycloalkyl, such as cyclopropyl;

$R^1$—N—$R^2$ together may be a pyrrolidino or piperidino residue;

A is a valyl, isoleucyl, leucyl, allo-isoleucyl, 2,2-dimethylglycyl, 2-cyclopropylglycyl, 2-cyclopentylglycyl, 3-tert-butylalanyl, 2-tert-butylglycyl, 3-cyclohexylalanyl, 2-ethylglycyl, 2-cyclohexylglycyl, norleucyl or norvalyl residue;

B is a N-alkyl-valyl, -norvalyl, -leucyl, -isoleucyl, -2-tert-butylglycyl, -3-tert-butylalanyl, -2-ethylglycyl, -2-cyclopropylglycyl, -2-cyclopentylglycyl, norleucyl or -2-cyclohexylglycyl residue where N-alkyl is preferably N-methyl or N-ethyl;

D is a prolyl, homoprolyl, hydroxyprolyl, 3,4-dehydroprolyl, 4-fluoroprolyl, 3-methylprolyl, 4-methylprolyl, 5-methylprolyl, azetidine-2-carbonyl, 3,3-dimethylprolyl, 4,4-difluoroprolyl, oxazolidine-4-carbonyl or thiazolidine-4-carbonyl residue;

E is a prolyl, homoprolyl, hydroxyprolyl, 3,4-dehydroprolyl, 4-fluoroprolyl, 3-methylprolyl, 4-methylprolyl, 5-methylprolyl, azetidine-2-carbonyl, 3,3-dimethylprolyl, 4,4-difluoroprolyl, oxazolidine-4-carbonyl or thiazolidine-4-carbonyl residue;

F and G are independently selected from the group consisting of prolyl, homoprolyl, hydroxyprolyl, thiazolidinyl-4-carbonyl, 1-aminopentyl-1-carbonyl, valyl, 2-tert-butylglycyl, isoleucyl, leucyl, 3-cyclohexylalanyl, phenylalanyl, N-methylphenylalanyl, tetrahydrosioquinolyl-2-histidyl, 1-aminoindyl-1-carbonyl, 3-pyridylalanyl, 2-cyclohexylglycyl, norleucyl, norvalyl, neopentylglycyl, trytophanyl, glycyl, 2,2-dimethylglycyl alanyl, β-alanyl and 3-naphthylalanyl residues;

X is hydrogen, alkyl (such as $C_1$–$C_5$), cycloalkyl (such as $C_3$–$C_7$), —$CH_2$-cyclohexyl or arylalkyl (such as benzyl or phenethyl);

s, t and u are independently 0 or 1; and K is hydroxy, alkoxy (such as $C_1$–$C_4$), phenoxy, benzyloxy or a substituted or unsubstituted amino moiety.

In addition, the compounds of Formula I can be present as a salt thereof with physiologically tolerated acids.

One subclass of compounds of this invention includes compounds of Formula I wherein $R^1$—N—$R^2$ is a pyrrolidinyl or piperidinyl residue.

Another subclass of compounds of this invention includes compounds of Formula I wherein K is an amino moiety of the formula $R^5$—N—$R^6$, wherein:

$R^5$ is hydrogen, or hydroxy, or $C_{1-7}$ alkoxy, or benzyloxy, or phenyloxy or $C_{1-12}$ linear or branched hydroxyalkyl, such as 3-hydroxy-1,1-dimethylpropyl, or $C_{1-7}$ linear or branched alkyl (which may be substituted by one or more fluoro atoms), or $C_{3-10}$-cycloalkyl, such as, bicyclo[3.3.0] octa-1yl, 1-methylcyclopentyl or 1-methylcyclohexyl; or benzyl (which may be substituted by up to three substituents which may independently be $CF_3$, nitro, $C_{1-7}$ alkylsulfonyl, $C_{1-4}$ alkoxy, phenoxy, benzoxy, halogen, $C_{1-4}$-alkyl, cyano, hydroxy, $N(CH_3)_2$, COOMe, COOEt, COOiPr, or $COONH_2$);

$R^6$ is hydrogen, or $C_{1-12}$ linear or branched alkyl (which may be substituted by one or more fluoro atoms), or $C_{1-12}$ linear or branched hydroxyalkyl, such as 3-hydroxy-1,1-dimethylpropyl, or $C_{3-10}$-cycloalkyl, such as bicyclo [3.3.0]octa-1-yl, or 1-methylcyclopentyl or 1-methylcyclohexyl; or —$(CH_2)_v$—$C_{3-7}$-cycloalkyl (v=0, 1,2, or 3), or norephedryl, or norpseudoephedryl, or quinolyl, or pyrazyl, or —$CH_2$-benzimidazolyl, or (1)-adamantyl, or (2)-adamantyl- —$CH_2$-adamantyl, or alpha-methyl-benzyl, or alpha-dimethylbenzyl, or —$(CH_2)_v$-phenyl (v=0,1,2, or 3; which may be substituted by up to two substituents which may independently be $CF_3$, nitro, $C_{1-7}$ alkylsulfonyl, $C_{1-4}$ alkoxy, phenoxy, benzoxy, halogen, $C_{1-4}$-alkyl which may form a cyclic system, cyano, hydroxy, $N(CH_3)_2$, COOMe, COOEt, COOiPr, or $COONH_2$), or —$(CH_2)_m$-naphthyl (m=0 or 1); or —$(CH2)_w$-benzhydryl (w=0,1, or 2); or biphenyl or picolyl or benzothiazolyl or benzoisothiazolyl or benzopyrazolyl or benzoxazolyl or —$(CH_2)_m$-fluorenyl (m=0 or 1); or pyrimidyl or —$(CH_2)$m-indanyl (m=0 or 1); or —$(CH_2CH_2O)_y$—$CH_3$ (y=0,1,2,3,4, or 5), or —$(CH_2CH_2O)_y$—$CH_2CH_3$ (y=0,1,2,3,4, or 5), or NH—$C_6H_5$ (which may be substituted by up to two substituents which may independently be $CF_3$, nitro, $C_{1-7}$ alkylsulfonyl, $C_{1-4}$ alkoxy, halogen, $C_{1-4}$ alkyl which may form a cyclic system, cyano, hydroxy, COOMe, COOEt, COOiPr, or $COONH_2$), or —$NCH_3$—$C_6H_5$ or —NH—$CH_2$—$C_6H_5$ or —$NCH_3$—$CH_2$—$C_6H_5$ or 5-membered heteroaryl which may be substituted by up to two substituents which may independently be $CF_3$, nitro, thiomethyl, thioethyl, $C_{3-6}$-cycloalkyl, —$CH_2$—COOEt, $C_{3-4}$-alkylene group forming a bicyclic system with the heterocycle, phenyl; or —$CHR^7$-5-membered heteroaryl (which may be substituted by up to two substituents which may independently be $CF_3$, nitro, cyano, halogen, COOMe, COOEt, COOiPr, $CONH_2$, $C_{1-4}$-alkyl, $C_{1-4}$-alkoxy, phenyl, benzyl, naphthyl, or $C_{1-7}$-alkylsulfonyl [$R^7$=hydrogen, linear or branched $C_{1-5}$ alkyl, benzyl; or $R^7$ and $R^5$ together form a group —$(CH_2)_3$— or —$(CH_2)_4$—).

This subclass includes compounds of Formula I wherein s, t and u are independently 0 or 1; $R^1$, $R^2$ and X are lower alkyl, A is a lower alkyl amino acid, B is a N-loweralkylated lower alkyl amino acid; D,E,F,G and K are as previously defined. With the foregoing in mind, three sets of such compounds can thus be depicted by the following formulas II, III, and IV:

$R^1R^2$N-CXH-CO-A-B-Pro-Pro-F-G-K          II $R^1R^2$N-CXH-CO-A-B-Pro-Pro-F-K          III $R^1R^2$N-CXH-CO-A-B-Pro-Pro-K          IV

—$CHR^7$-5-membered heteroaryl may, for example, be represented by one of the following residues:

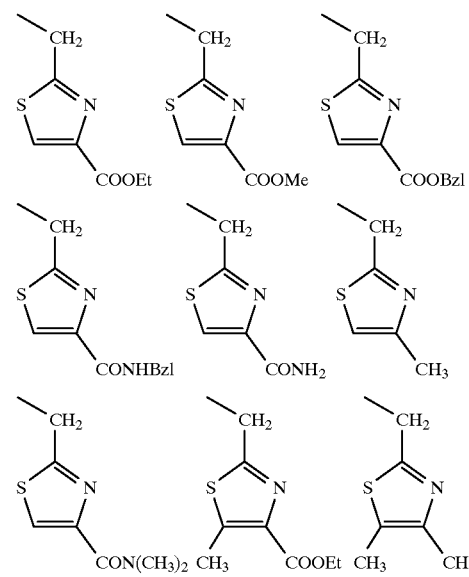

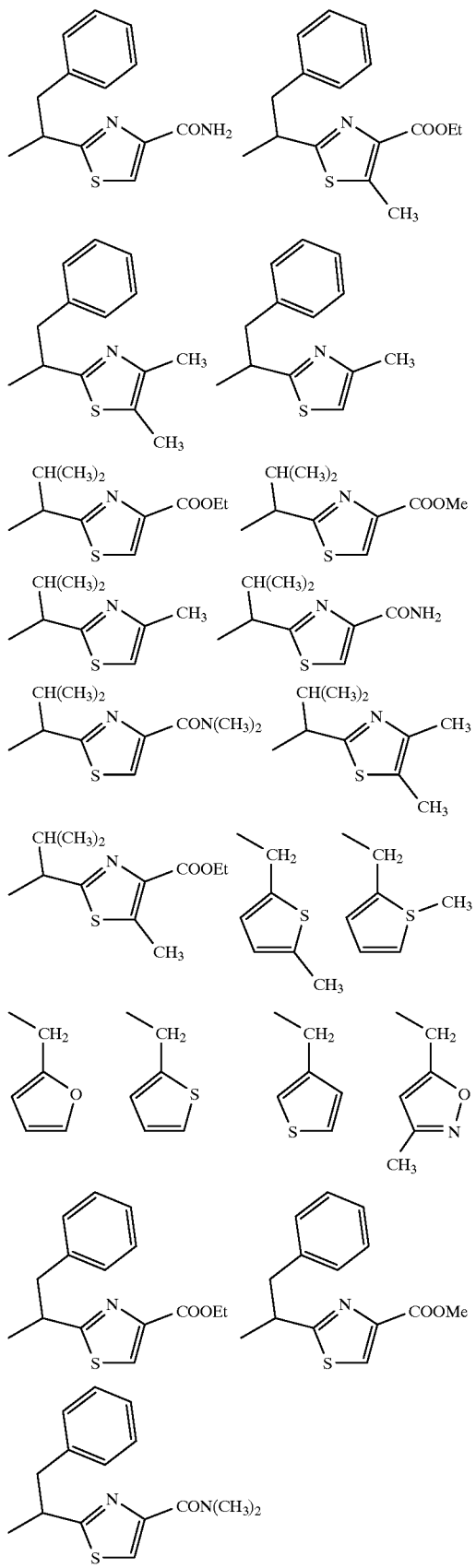
—NR⁵CHR⁷-5-membered heteroaryl may, for example, be represented by the following residues:
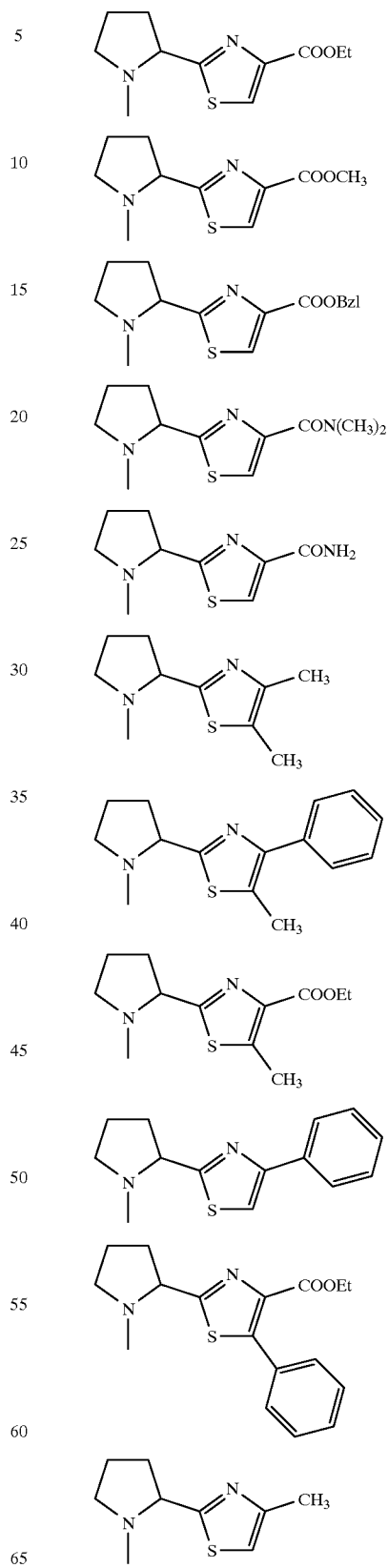

5-membered heteroaryl may, for example, be represented by the following residues:
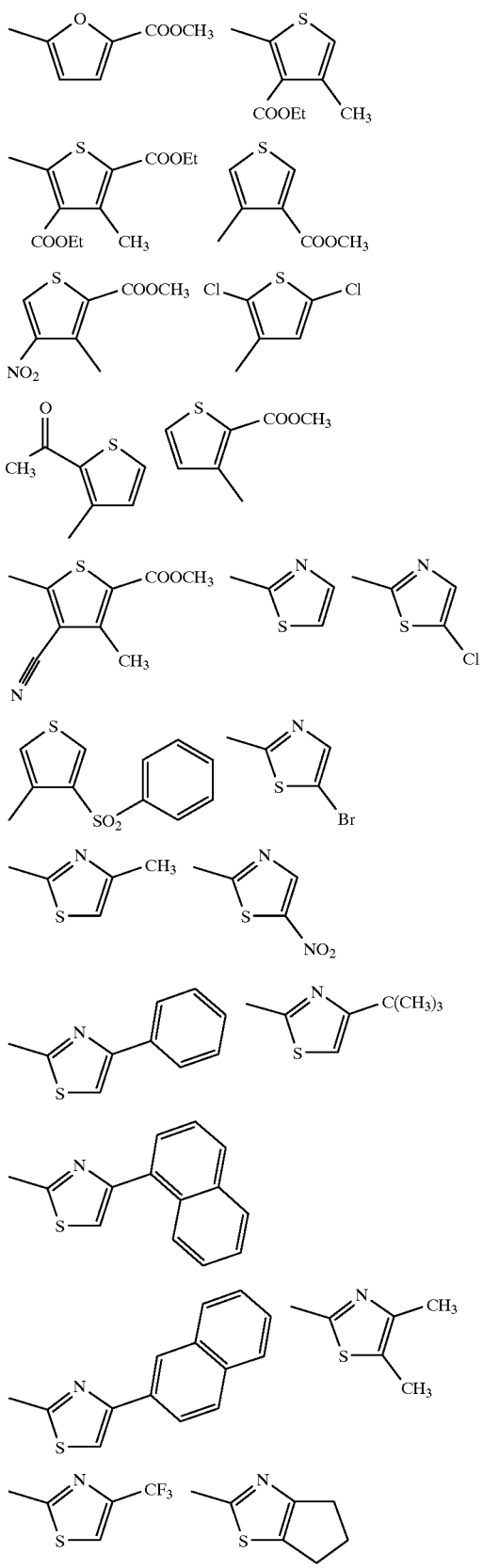
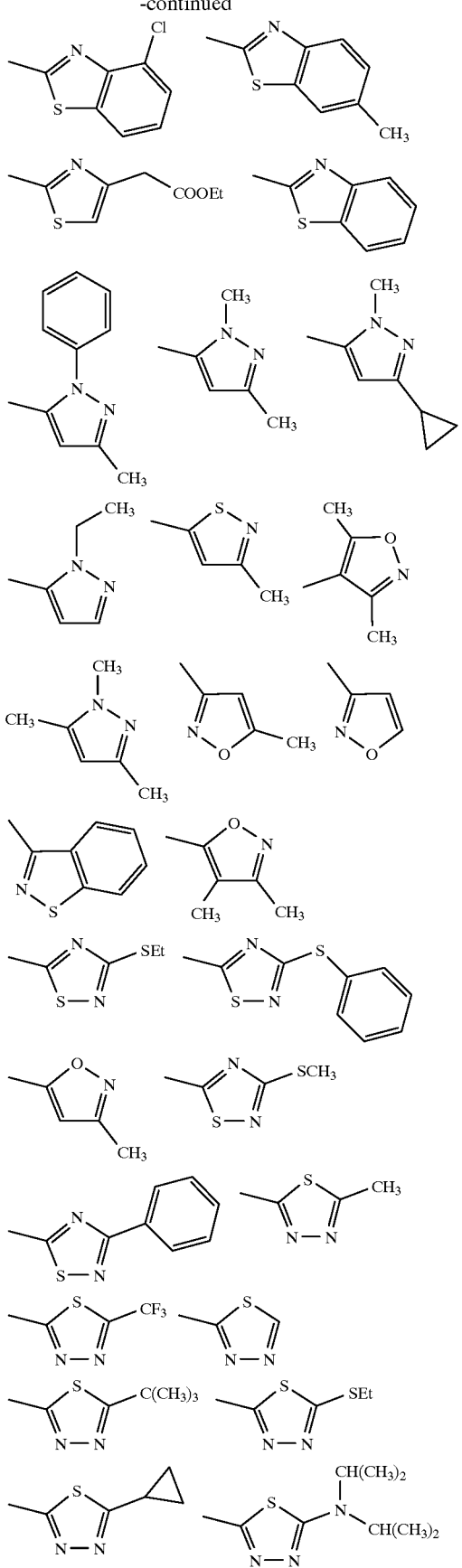

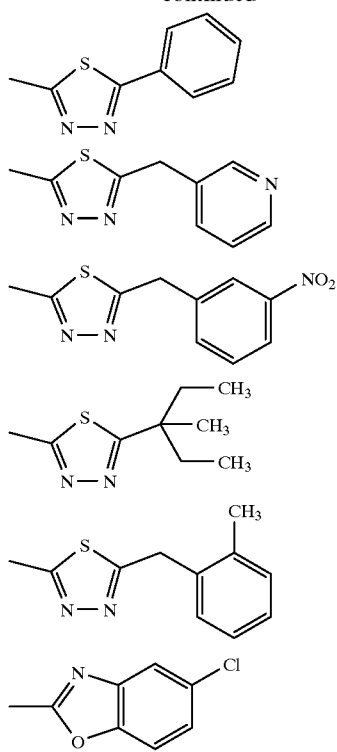

In another subclass of compounds of this invention R⁵—N—R⁶ together may form structures selected from the group consisting of:

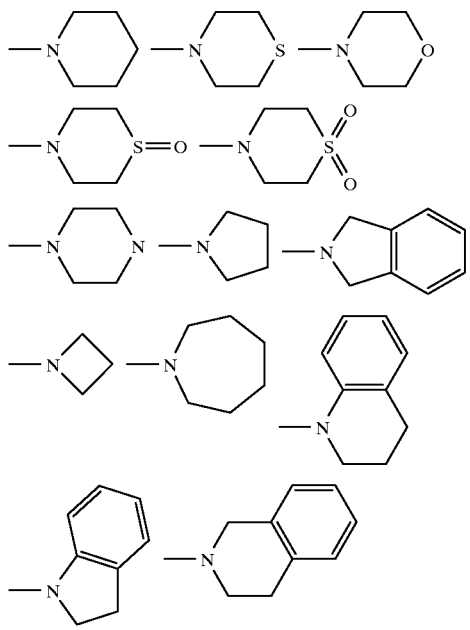

Still another subclass of compounds of this invention includes, for example, compounds of Formula I wherein s, t and u are 1 and K is a hydroxy, alkoxy, phenoxy or benzyloxy moiety.

Yet another subclass of compounds of this invention includes, for example, compounds of Formula I wherein s and t are 1, u is 0 and K is a hydroxy, alkoxy, phenoxy or benzyloxy moiety.

Another subclass of compounds of this invention includes, for example, compounds of Formula I wherein s is 1, t and u are 0 and K is a hydroxy, alkoxy, phenoxy or benzyloxy moiety.

In particular embodiments, a compound of Formula I is one in which $R^1$ and $R^2$ are each methyl or ethyl; X is isopropyl, sec-butyl or tert-butyl; s is 1; t and u are each 0; A is valyl, isoleucyl or 2-tert-butylglycyl; B is N-methylvalyl, 1-isoleucyl or -2-tert-butylglycyl; D is prolyl, thiazolidinyl-4-carbonyl or 3,4 dehydroprolyl; E is prolyl, thiazolidinyl-4-carbonyl, homoprolyl, 3,4-dehydroprolyl or hydroxyprolyl; and K is a substituted or unsubstituted amino moiety having the formula $R^5$—N—$R^6$.

In a further embodiment, the Dolastatin-15 derivative is a compound of Formula I in which $R^1$ and $R^2$ are each methyl or ethyl; X is isopropyl, sec-butyl or tert-butyl; s is 1; t and u are each 0; A is valyl, isoleucyl or 2-tert-butylglycyl; B is N-methylvalyl, 1-isoleucyl or 2-tertbutylglycyl; D is prolyl, thiazolidinyl-4-carbonyl, or 3,4-dehydroprolyl; E is prolyl, thiazolidinyl-4-carbonyl, homoprolyl, 3,4-dehydroprolyl or hydroxyprolyl; and K is a substituted amino moiety having the formula $R^5$—N—$R^6$ wherein $R^5$ is hydrogen or $C_1$-$C_4$ alkoxy and $R^6$ is a $C_1$-$C_{12}$ linear or branched alkyl group or a $C_1$-$C_{12}$ linear or branched hydroxyalkyl group represented, for example, by the following monovalent radicals:

—C(CH₃)₂—CH₂—CH₂—OH, also referred to as 3-hydroxy-1,1-dimethylpropyl;

—C(CH₃)₃, also referred to as tert-butyl;

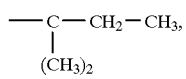

also referred to as 1,1-dimethyl propyl;

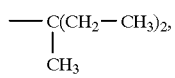

also referred to as 1-methyl-1-ethyl propyl;

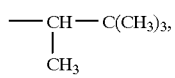

also referred to as (S)- or (R)-1-methyl-2,2-dimethyl propyl;

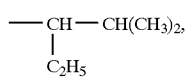

also referred to as (S)- or (R)-1-ethyl-2-methyl propyl;

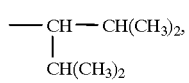

also referred to as 1-isopropyl-2-methyl butyl; or

—C(CH₃)₂—CH(CH₃)₂, also referred to as 1,1-dimethyl-2-methyl propyl

—CH(CH₃)₂, also referred to as isopropyl

—CH(CH$_3$)CH$_2$CH$_3$, also referred to as sec-butyl, (S)- or (R)-
—CH(CH$_3$)CH(CH$_3$)$_2$, also referred to as 1,2-dimethylpropyl.

In another embodiment, the Dolastatin-15 derivative of the invention is a compound of Formula I in which R$^1$ and R$^2$ are each methyl or ethyl; X is isopropyl, sec-butyl or tert-butyl; s is 1; t and u are each 0; A is valyl, isoleucyl or 2-tert-butylglycyl; B is N-methylvalyl, 1-isoleucyl or 2-tert-butylglycyl; D is prolyl, thiazolidinyl-4-carbonyl, 3,4-dehydroprolyl; E is prolyl, thiazolidinyl-4-carbonyl, homoprolyl, 3,4-dehydroprolyl or hydroxyprolyl; and K is a substituted amino moiety having the formula R$^5$—N—R$^6$ wherein R$^5$ is hydrogen or C$_1$–C$_4$ alkoxy and R$^6$ is a monovalent radical such as a C$_3$–C$_{10}$ cycloalkyl group (e.g. cyclobutyl, cyclopentyl, cyclohexyl, or 1-methylcyclopentyl, or 1-methylcyclohexyl or bicyclo [3.3.0]octa-1-yl); a (1)- or (2)-adamantyl group; (CH$_2$)v-phenyl with v=1 or α,α-dimethylbenzyl.

Figure 2:
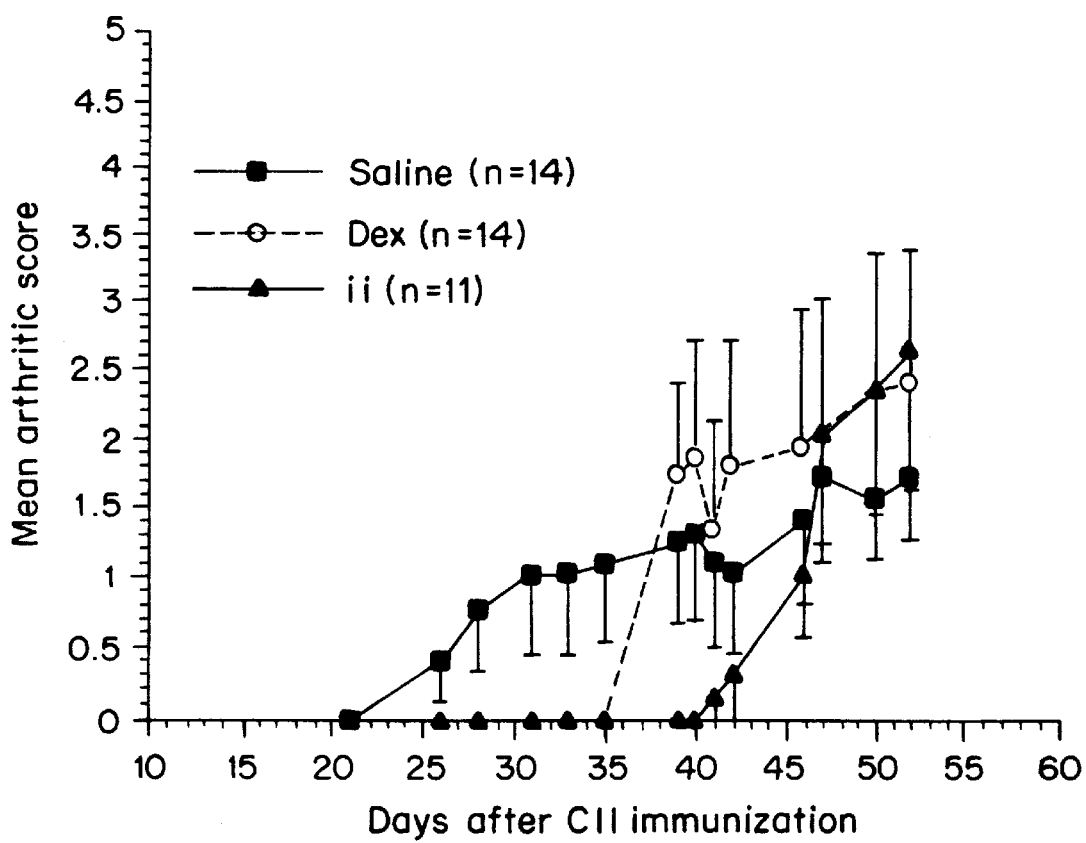
FIG. 2 is a graph showing mean arthritic score as a function of the number of days after immunization with type II collagen, for mice treated with saline (control), dexamethasone (standard therapy) and compound ii from FIG. 1A. Treatment was commenced on day 26 post-immunization and was terminated on day 35 post-immunization.
Figure 3:
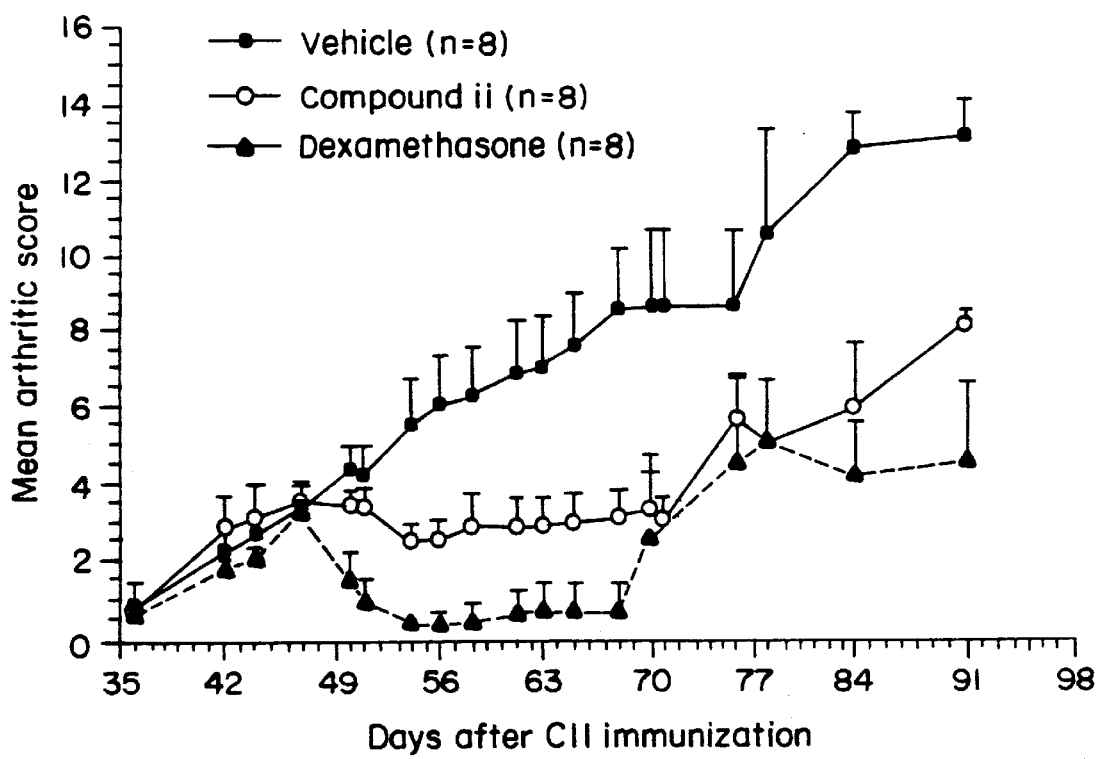
FIG. 3 is a graph showing mean arthritic score as a function of the number of days after immunization with type II collagen, for mice treated with vehicle (control), dexamethasone (standard therapy) and compound ii from FIG. 1A. Treatment was commenced on day 48 post immunization and lasted for 21 days.

In a further embodiment, the Dolastatin-15 derivative of the invention is a compound of Formula I in which R$^1$ and R$^2$ are each methyl; X is isopropyl; s is 1; t and u are each 0; A is valyl; B is N-methylvalyl; D is prolyl; E is prolyl; and K is a substituted amino moiety having the formula R$^5$—N—R$^6$ wherein R$^5$ is hydrogen and R$^6$ is a tert-butyl group. This compound corresponds to compound ii depicted in FIG. 1A. The results of the use of compound ii of Formula I, are described in Examples 3 and 4 and represented graphically in FIGS. 2, 3 and 4.

The Dolastatin-15 derivative of the present invention can optionally be administered in a pharmaceutically acceptable carrier. Pharmaceutically acceptable carriers are well known to those who are skilled in the art. The choice of a carrier will be determined in part by the particular compound of Formula I, as well as by the particular method used to administer the Dolastatin-15 derivative.

Also the subject of this invention are pharmaceutical composition which comprise one or more Dolastatin-15 derivatives of Formula I either alone or in combination with one or more other antiarthritic drugs, such as those described herein. The pharmaceutical composition can optionally include a pharmaceutically acceptable carrier, diluent or a compound which aids in processing, for example, binders, fillers and preservatives.

In another aspect, the present invention comprises a method for the treatment of rheumatoid arthritis in a mammal using the Dolastatin-15 derivatives of Formula I. For purposes of this invention the phrases "method of treatment of rheumatoid arthritis" and "suppression of rheumatoid arthritis" can be used interchangeably. As used herein, the term "suppression" includes any or all of the following: (1) amelioration of existing symptoms; (2) prevention or slowing of progression of symptoms; (3) prevention or delay of the inception or occurrence of the disease in a susceptible subject, i.e., prophylaxis.

The method of treatment of the present invention comprises administering a therapeutically effective amount of one or more compounds of Formula I. The compounds of Formula I can be administered alone or with a pharmaceutically accepted carrier or diluent appropriate for the desired route of administration. Administration can be by any of the means which are conventional for pharmaceuticals, including oral and parenteral means such as subcutaneously, intravenously, intramuscularly, intraperitoneally, nasally or rectally. Such pharmaceutical compositions may also contain other therapeutically active ingredients.

In another aspect of the invention one or more Dolastatin-15 derivatives are administered either alone or in combination with one or more other antiarthritic drugs in a mammal having or susceptible to rheumatoid arthritis. Administration of one or more Dolastatin-15 derivative(s) in combination with one or more other antiarthritic drugs enhances treatment of rheumatoid arthritis. For example, a combination provides greater suppression or fewer side effects, and/or can make it possible to administer a lower dose of the known antiarthritic drug to produce the same effect. The other antiarthritic drug can be, but is not limited to, the following: (1) a nonsteroidal anti-inflammatory agent such acetylsalicylic (aspirin), ibuprofen, or naproxen; (2) an organic gold derivative such a gold sodium thiomalate, aurothioglucose, or auranofin; (3) D-pencillamine; (4) a 4-aminoquinoline agent such as hydroxychloroquine; (5) azathioprine; (6) methotrexate; (7) cyclosporin; (8) an angiogenesis inhibitor such as AGM-1470 (Ingber, et al., *Nature* 348, (1990) 555); (9) monoclonal antibodies to T cells; (10) monoclonal antibodies to adhesion molecules; (11) monoclonal antibodies to cytokines and growth factors; (12) Tumor Necrosis Factor Receptor (TNFR)-IgG; (13) IL-1 receptor antagonists; and ICE inhibitors.

In a specific embodiment, at least two or more Dolastatin-15 derivatives are administered either alone or in combination with one or more other antiarthritic drugs to a mammal having or susceptible to rheumatoid arthritis.

The dosage administered to the mammal, such as a human, includes a therapeutically effective amount of a compound of Formula I, as described herein. The dosage can be determined empirically, using known methods, and will depend upon factors such as the biological activity, mechanism of action, toxicity profile of the particular compounds employed; the means of administration; the age, health and body weight of the recipient; the nature duration and extent of the symptoms; the frequency of treatment; the administration of other therapies; and the effect desired.

A typical daily dose of the compounds of Formula I will be from about 1 to about 100 milligrams per kilogram of body weight by oral administration and from about 1 to about 100 milligrams per kilogram of body weight by parenteral administration.

The Dolastatin-15 derivatives of the present invention can be administered in conventional solid or liquid pharmaceutical forms, for example, uncoated or (film)coated tablets, capsules, powders, granules, suppositories or solutions. These are produced in a conventional manner. The active substances can for this purpose be processed with conventional pharmaceutical aids such as tablet binders, fillers, preservatives, tablet disintegrants, flow regulators, plasticizers, wetting agents, dispersants, emulsifiers, solvents, sustained release compositions, antioxidants and/or propellant gases (cf. H. Sücker et al.: Pharmazeutische Technologie, Thieme-Verlag, Stuttgart, 1978). The administration forms obtained in this way typically contain from about 1 to about 90% by weight of the active substance.

If more than one Dolastatin-15 derivative is administered, they can be administered at the same time (simultaneously) or at separate times (sequentially), provided that they are administered in such an order and at intervals appropriate to produce the desired therapeutic effect. If two or more Dolastatin-15 derivatives are administered at the same time, they can be given separately (as individual derivatives) or in physical combination (as a mixture or combination). The same is the case when one or more Dolastatin-15 derivatives are administered with one or more other antiarthritic drugs. They can be administered simultaneously or sequentially and individually or as a combination or mixture. Pharmaceutical compositions which include one or more Dolastatin-15 derivatives or one or more Dolastatin-15 derivatives and one or more other antiarthritic drugs are also the subject of this invention.

The compounds of Formula I are described in detail above. In a particular embodiment, the method of the invention uses a Dolastatin-15 derivative of Formula I in which $R^1$ and $R^2$ are each methyl or ethyl; X is isopropyl, sec-butyl or tert-butyl; s is 1; t and u are each 0; A is valyl, isoleucyl or 2-tert-butylglycyl; B is N-methylvalyl, 1-isoleucyl or 2-tert-butylglycyl; D is prolyl, thiazolidinyl-4-carbonyl or 3,4-dehydroprolyl; E is prolyl, thiazolidinyl-4-carbonyl, homoprolyl, 3,4-dehydroprolyl or hydroxyprolyl; and K is a substituted or unsubstituted amino moiety having the formula $R^5$—N—$R^6$.

In a further embodiment, the method of the invention uses a Dolastatin-15 derivative of Formula I in which $R^1$ and $R^2$ are each methyl or ethyl; X is isopropyl, sec-butyl or tert-butyl; s is 1; t and u are each 0; A is valyl, isoleucyl or 2-tert-butylglycyl; B is N-methylvalyl, 1-isoleucyl or 2-tert-butylglycyl; D is prolyl, thiazolidinyl-4-carbonyl or 3,4-dehydroprolyl; E is prolyl, thiazolidinyl-4-carbonyl, homoprolyl, 3,4-dehydroprolyl or hydroxyprolyl; and K is a substituted amino moiety having the formula $R^5$—N—$R^6$ wherein $R^5$ is hydrogen or $C_1$–$C_4$ alkoxy and $R^6$ is a $C_1$–$C_{12}$ linear or branched alkyl group or $C_1$–$C_{12}$ linear or branched hydroxyalkyl group represented, for example, by the following monovalent radicals:

—C(CH$_3$)$_2$—CH$_2$—CH$_2$—OH, also referred to as 3-hydroxy-1,1-dimethylpropyl;

—C(CH$_3$)$_3$, also referred to as tert-butyl;

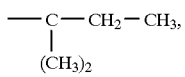

also referred to as 1,1-dimethyl propyl;

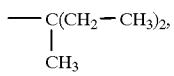

also referred to as 1-methyl-1-ethyl propyl;

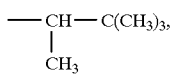

also referred to as (S)- or (R)-1-methyl-2,2-dimethyl propyl;

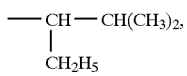

also referred to as (S)- or (R)-1-ethyl-2-methyl propyl;

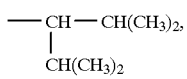

also referred to as 1-isopropyl-2-methyl butyl; or
—C(CH$_3$)$_2$—CH(CH$_3$)$_2$, also referred to as 1,1-dimethyl-2-methyl propyl
—CH(CH$_3$)$_2$, also referred to as isopropyl —CH(CH$_3$)CH$_2$CH$_3$ also referred to as sec-butyl, (S)- or (R)-
—CH(CH$_3$)CH(CH$_3$)$_2$, also referred to as 1,2-dimethylpropyl.

In another embodiment, the method of the invention uses a compound of Formula I in which $R^1$ and $R^2$ are each methyl or ethyl; X is isopropyl, sec-butyl or tert-butyl; s is 1; t and u are each 0; A is valyl, isoleucyl or 2-tert-butylglycyl; B is N-methylvalyl, 1-isoleucyl or 2-tert-butylglycyl; D is prolyl, thiazolidinyl-4-carbonyl, 3,4-dehydroprolyl; E is prolyl, thiazolidinyl-4-carbonyl, homoprolyl, 3,4-dehydroprolyl or hydroxyprolyl; and K is a substituted amino moiety having the formula $R^5$—N—$R^6$ wherein $R^5$ is hydrogen or $C_1$–$C_4$ alkoxy and $R^6$ is a monovalent radical such as a $C_3$–$C_{10}$ cycloalkyl group (e.g. cyclobutyl, cyclopentyl, cyclohexyl, 1-methylcyclopentyl, 1-methylcyclohexyl or bicyclo[3.3.0]octa-1-yl); a (1)- or (2)-adamantyl group; (CH$_2$)v-phenyl with v=1 or α,α-dimethylbenzyl.

In a further embodiment, the method of the invention uses a Dolastatin-15 derivative of Formula I in which $R^1$ and $R^2$ are each methyl; X is isopropyl; s is 1; t and u are each 0; A is valyl; B is N-methylvalyl; D is prolyl; E is prolyl; and K is a substituted amino moiety having the formula $R^5$—N—$R^6$ wherein $R^5$ is hydrogen and $R^6$ is a tert-butyl group. This compound corresponds to compound ii depicted in the FIG. 1A. The use of compound ii in the treatment of rheumatoid arthritis is described in Examples 3 and 4 with results presented in FIGS. 2, 3 and 4.

Synthetic Methods

The compounds of Formula I can be prepared by known methods of peptide synthesis such as those described herein and, in U.S. patent application Ser. No. 08/470,453 filed Jun. 7, 1995, the teachings of which are incorporated herein by reference. The peptides can be assembled sequentially from individual amino acids or by linking suitable small peptide fragments. In sequential assembly, the peptide chain is extended stepwise, starting at the C-terminus, by one amino acid per step. In fragment coupling, fragments of different lengths can be linked together, and the fragments can also be obtained by sequential assembly from amino acids or by fragment coupling of still shorter peptides.

In both sequential assembly and fragment coupling it is necessary to link the units by forming an amide linkage, which can be accomplished via a variety of enzymatic and chemical methods. The methods described herein for formation of peptidic amide linkages, are also suitable for the formation of non-peptidic amide linkages.

Chemical methods for forming the amide linkage are described in detail in standard references on peptide chemistry, including Müller, *Methoden der organischen Chemie* Vol. XV/2, 1–364, Thieme Verlag, Stuttgart, (1974); Stewart and Young, *Solid Phase Peptide Synthesis*, 31–34 and 71–82, Pierce Chemical Company, Rockford, Ill. (1984); Bodanszky et al., *Peptide Synthesis*, 85–128, John Wiley & Sons, New York, (1976); *Practice of Peptide Synthesis*, M. Bodansky, A. Bodansky, Springer-Verlag, 1994 and other standard works in peptide chemistry. Preferred methods include the azide method, the symmetric and mixed anhydride method, the use of in situ generated or preformed active esters, the use of urethane protected N-carboxy anhydrides of amino acids and the formation of the amide linkage using coupling reagents, such as dicyclohexylcarbodiimide (DCC), diisopropylcarbodiimide (DIC), 1-ethoxycarbonyl-2-ethoxy-1,2-dihydroquinoline (EEDQ), pivaloyl chloride, 1-ethyl-3-(3-dimethylaminopropyl) carbodiimide hydrochloride (EDCI), n-propane-phosphonic anhydride (PPA), N,N-bis (2-oxo-3-oxazolidinyl)amido phosphoryl chloride (BOP-Cl), bromo-tris-pyrrolidinophosphonium hexafluorophosphate (PyBrop), diphenylphosphoryl azide (DPPA), Castro's reagent (BOP, PyBop), O-benzotriazolyl-N,N,N',N'-tetramethyluronium salts (HBTU), O-azabenzotriazolyl-N,N,N',N'-tetramethyluronuim salts (TATU), diethylphosphoryl cyanide (DEPCN), 2,5-diphenyl-2,3-dihydro-3-oxo-4-hydroxythiophene dioxide (Steglich's reagent; HOTDO), and 1,1'-carbonyldiimidazole (CDI). The coupling reagents can be employed alone or in combination with additives such as N,N-dimethyl-4-aminopyridine (DMAP), N-hydroxy-benzotriazole (HOBt), N-hydroxybenzotriazine (HOOBt), N-hydroxysuccinimide (HOSu) or 2-hydroxypyridine.

Although the use of protecting groups is generally not necessary in enzymatic peptide synthesis, reversible protection of reactive groups not involved in formation of the amide linkage is necessary for both reactants in chemical synthesis. Three conventional protective group techniques typically used for chemical peptide synthesis are: the benzyloxycarbonyl (Z), the t-butoxycarbonyl (Boc) and the 9-fluorenylmethoxycarbonyl (Fmoc) techniques. Identified in each case is the protective group on the α-amino group of the chain-extending unit. A detailed review of amino-acid protective groups is given by Müller, *Methoden der organischen Chemie* Vol. XV/1, pp 20–906, Thieme Verlag, Stuttgart (1974).

The units employed for assembling the peptide chain can be reacted in solution, in suspension or by a method similar to that described by Merrifield in *J. Amer. Chem. Soc.* 85 (1963) 2149. In one method, peptides are assembled sequentially or by fragment coupling using the Z, Boc or Fmoc protective group technique, with one of the reactants in the Merrifield technique being bonded to an insoluble polymeric support (also called resin hereinafter). This typically entails assembling the peptide sequentially on the polymeric support using the Boc or Fmoc protective group technique, with the growing peptide chain covalently bonded at the C terminus to the insoluble resin particles. This procedure allows the removal of reagents and by-products by filtration, eliminating the need to recrystallize intermediates.

The protected amino acids can be linked to any suitable polymer, which must be insoluble in the solvents used and have a stable physical form which permits filtration. The polymer must contain a functional group to which the first protected amino acid can be covalently attached. A wide variety of polymers are suitable for this purpose, for example, cellulose, polyvinyl alcohol, polymethacrylate, sulfonated polystyrene, chloromethylated styrene/divinylbenzene copolymer (Merrifield resin), 4-methylbenzhydrylamine resin (MBHA-resin), phenylacetamidomethyl resin (Pam-resin), p-benzyloxy-benzyl-alcohol-resin, benzhydryl-amine-resin (BHA-resin), 4-(hydroxymethyl)-benzoyl-oxymethyl-resin, the resin of Breipohl et al. (*Tetrahedron Letters* 28 (1987) 565; supplied by BACHEM), 4-(2,4-dimethoxyphenylaminomethyl) phenoxy resin (supplied by Novabiochem) or o-chlorotrityl-resin (supplied by Biohellas).

Solvents suitable for peptide synthesis include any solvent which is inert under the reaction conditions, for example, water, N,N-dimethylformamide (DMF), dimethyl sulfoxide (DMSO), acetonitrile, dichloromethane (DCM), 1,4-dioxane, tetrahydrofuran (THF), N-methyl-2-pyrrolidone (NMP) and mixtures of these solvents.

Peptide synthesis on the polymeric support can be carried out in a suitable inert organic solvent in which the amino acid derivatives and starting materials employed are soluble. Particularly useful solvents are, for example, DMF, DCM, NMP, acetonitrile, DMSO and mixtures thereof, due to their resin swelling properties.

Following synthesis, the peptide is removed (commonly referred to as cleaved) from the polymeric support. The conditions under which this cleavage is accomplished are well known in the art of peptide synthesis and depend in part on the type of resin employed. The cleavage reactions most commonly used are acid- or palladium-catalyzed, the acid catalyzed cleavage being conducted in, for example, liquid anhydrous hydrogen fluoride, anhydrous trifluoromethanesulfonic acid, dilute or concentrated trifluoroacetic acid, and acetic acid/dichloromethane/trifluoroethanol mixtures. The palladium-catalyzed cleavage can be carried out in THF or THF-DCM-mixtures in the presence of a weak base such as morpholine. Certain protecting groups are also cleaved off under these conditions.

Partial deprotection of the peptide may also be necessary prior to certain derivatization reactions. For example, peptides dialkylated at the N-terminus can be prepared either by coupling the appropriate N,N-di-alkylamino acid to the peptide in solution or on the polymeric support or by reductive alkylation of the resin-bound peptide in DMF/1% acetic acid with $NaCNBH_3$ and the appropriate aldehyde or by hydrogenation of the peptide in solution in the presence of aldehyde or ketone and Pd/C.

The various non-naturally occurring amino acids as well as the various non-amino acid moieties disclosed herein may be obtained from commercial sources or synthesized from commercially-available materials using methods known in the art. For example, amino acid building blocks with $R^1$ and $R^2$ moieties can be prepared according to E. Wuensch, Huben Weyl, *Methoden der organischen Chemie* Vol. XV/1, p. 306, Thieme Verlag, Stuttgart (1974) and literature cited therein. Peptides with gamma-or delta-lactam bridges can be prepared by incorporating the appropriate lactam-bridged dipeptide units (R. Freidinger, *J. Org. Chem.* (1982) 104–109) into the peptide chain. Peptides with thiazole-, oxazol-, thiazolin- or oxazolin-containing dipeptide building blocks can be prepared by incorporating the appropriate dipeptidic units (P. Jouin et al., *Tetrahedron Letters* (1992), pp. 2087–2810; P. Wipf et al., *Tetrahedon Letters* (1992), pp. 907–910; W. R. Tully, *J. Med. Chem.* (1991), p 2060–2065; U. Schmidt et al., *Synthesis* (1987), pp 233–236) into the peptide chain.

The following procedures are intended to illustrate methods useful for preparation of compounds of Formula I. When applicable, amino acids are abbreviated using the known three letter codes. Other meanings used are: $Me_2Val$=N,N-dimethylvaline, MeVal=N-methylvaline, TFA=trifluoroacetic acid, Ac=acetic acid, Bu=butyl, Et=ethyl, Me=methyl, Bzl=benzyl, Nal=3-naphthylalanine, Cha=3-cyclohexylalanine, Npg=neopentyl glycine, Abu=2-amino butyryl, Dab=2,4-diaminobutyryl, iPr=isopropyl General Synthetic Procedures I. Compounds of Formula I of the present invention are either synthesized by classical solution synthesis using standard Z- and Boc-methodology as described above or by standard methods of solid-phase synthesis on a completely automatic model 431A synthesizer supplied by APPLIED BIOSYSTEMS. The apparatus uses different synthetic cycles for the Boc and Fmoc protective group techniques.

In the case of solid phase synthesis, the N,N-dialkyl-penta- or hexapeptide acids are liberated from the solid support and further coupled with the corresponding C-terminal amines in solution. BOP-Cl and PyBrop were used as reagents for coupling of the amino acid following the N-methylamino acids. The reaction times were correspondingly increased. For reductive alkylation of the N-terminus, the peptide-resin was deprotected at the N terminus and then reacted with a 3-fold molar excess of aldehyde or ketone in DMF/1% acetic acid with addition of 3 equivalents of $NaCNBH_3$. After the reaction was complete (negative Kaiser test) the resin was washed several times with water, isopropanol, DMF and dichloromethane.

In solution synthesis, the use of either Boc-protected amino acid NCAs (N-tert-butyloxycarbonyl-amino acid-N-carboxy-anhydrides), Z-protected amino acid NCAs (N-benzyloxycarbonyl-amino acid-N-carboxy-anhydrides), or the use of pivaloylchloride as condensing agent respectively is most advantageous for coupling of the amino acid following the N-methylamino acids. Reductive alkylation of the N terminus can, for example, be achieved by reaction of the N-terminally deprotected peptides or amino acids with the corresponding aldehydes or ketones using $NaCNBH_3$ or hydrogen, Pd/C.

| a) | Synthetic cycle for the Boc protective group technique: | |
|---|---|---|
| 1. | 30% trifluoroacetic acid in DCM | 1 × 3 min |
| 2. | 50% trifluoroacetic acid in DCM | 1 × 1 min |
| 3. | DCM washing | |
| 4. | 5% diisopropylethylamine in DCM | 5 × 1 min |
| 5. | 5% diisopropylethylamine in NMP | 1 × 1 min |
| 6. | NMP washing | 5 × 1 min |
| 7. | Addition of preactivated protected amino acid (DCC and 1 equivalent of HOBt in NMP/DCM); Peptide coupling (1st part) | 1 × 30 min |
| 8. | Addition of DMSO to the reaction mixture until it contains 20% DMSO by volume; Peptide coupling (2nd part) | 1 × 16 min |
| 9. | Addition of 3.8 equivalents of diisopropylethylamine to the reaction mixture; Peptide coupling (3rd part) | 1 × 7 min |
| 10. | DCM washing | 3 × 1 min |
| 11. | If conversion is incomplete, repetition of coupling (back to 6) | |
| 12. | 10% acetic anydride, 5% diisopropylethylamine in DCM | 1 × 2 min |
| 13. | 10% acetic anhydride in DCM | 1 × 4 min |
| 14. | DCM washing | 4 × 1 min |
| 15. | Back to 1. | |

BOP-Cl and PyBrop were used as reagents for coupling of the amino acid following N-methylamino acids. The reaction times were correspondingly increased. In solution synthesis, the use of either Boc-protected amino acid NCAs (N-tert-butyloxycarbonyl-amino acid-N-carboxy-anhydrides) or Z-protected amino acids NCAs respectively is most advantageous for this type of coupling.

| b) | Synthetic cycle for the Fmoc protective group technique: | |
|---|---|---|
| 1. | DMF washing | 1 × 1 min |
| 2. | 20% piperidine in DMF | 1 × 4 min |
| 3. | 20% piperidine in DMF | 1 × 16 min |
| 4. | DMF washing | 5 × 1 min |
| 5. | Addition of the preactivated protected amino acid (activation by 1 equivalent of TBTU and 5 equivalents of DIPEA in DMF); Peptide coupling | 1 × 61 min |
| 6. | DMF washing | 3 × 1 min |
| 7. | If conversion is incomplete, repetition of coupling (back to 5) | |

-continued

| b) | Synthetic cycle for the Fmoc protective group technique: | |
|---|---|---|
| 8. | 10% acetic anhydride in DMF | 1 × 8 min |
| 9. | DMF washing | 3 × 1 min |
| 10. | Back to 2. | |

OP-Cl and PyBrop were used as reagents for coupling on the amino acid following the N-methylamino acids. The reaction times were correspondingly increased.

II. Reductive Alkylation of the N-terminus

The peptide-resin prepared in Ia or Ib above was deprotected at the N-terminus (steps 2–4 in Ib or 1–6 in 1a) and then reacted with a 3-fold molar excess of aldehyde or ketone in DMF/1% acetic acid with addition of 3 equivalents of $NaCNBH_3$. After reaction was complete (negative Kaiser test) the resin was washed several times with water, isopropanol, DMF and dichloromethane.

III. Workup of the Peptide-resins Obtained as in Ia and II

The peptide-resin was dried under reduced pressure and transferred into a reaction vessel of a TEFLON HF apparatus (supplied by PENINSULA). Addition of a scavenger, for example, anisole (1 ml/g of resin), and in the case of tryptophan-containing peptides of a thiol to remove the indolic formyl group, for example, ethanedithiol (0.5 ml/g of resin), was followed by condensing in hydrogen fluoride (10 ml/g of resin) while cooling with liquid $N_2$. The mixture was allowed to warm to 0° C. and stirred at this temperature for 45 minutes. The hydrogen fluoride was then stripped off under reduced pressure, and the residue was washed with ethyl acetate in order to remove remaining scavenger. The peptide was extracted with 30% acetic acid and filtered, and the filtrate was lyophilized.

IV. Work-up of the Peptide-resins Obtained as in Ib and II

The peptide-resin was dried under reduced pressure and then subjected to one of the following cleavage procedures, depending on the amino acid composition (Wade, Tregear, Howard Florey Fmoc Workshop Manual, Melbourne 1985).

| | TFA | Scavenger | Reaction time |
|---|---|---|---|
| 1. | 95% | 5% water | 1.5 h |
| 2. | 95% | 5% ethanethiol/ anisole (1:3) | 1.5 h |

The suspension of the peptide-resin in the suitable TFA mixture was stirred at room temperature for the stated time and then the resin was filtered off and washed with TFA and DCM. The filtrate and the washings were concentrated, and the peptide was precipitated by addition of the diethyl ether. After cooling in an ice bath, the precipitate was filtered off, taken up in 30% acetic acid and lyophilized.

V. When an o-chlorotrityl-resin (supplied by Biohellas) is used, the suspension of the peptide-resin in an acetic acid/trifluoroethanol/dichloromethane mixture is stirred at room temperature for 1 h. The 566X(1:1 resin is then filtered off with suction and thoroughly washed with the cleavage solution. The combined filtrates are concentrated in vacuo and treated with water. The precipitated solid is removed by filtration or centrifugation, washed with diethyl ether and dried under reduced pressure.

VI. Purification and Characterization of the Peptides

Purification was carried out by gel chromatography (SEPHADEX G-10, G-15/10% HOAc, SEPHADEX LH20/MeOH) medium pressure chromatography (stationary phase: HD-SIL C-18, 20–45 micron, 100 Angstrom; mobile phase: gradient with A=0.1% TFA/MeOH, B=0.1% TFA/ water) or preparative HPLC (stationary phase: water Delta-Pak C-18, 15 micron, 100 Angstrom; mobile phase: gradient with A=0.1% TFA/MeOH, B=0.1% TFA/water).

The purity of the resulting products was determined by analytical HPLC (stationary phase: 100 2.1 mm VYDAC C-18, 51, 300 Angstrom; mobile phase: acetonitrile-water gradient, buffered with 0.1% TFA, 40° C.)

Characterization was by amino acid analysis and fast atom bombardment mass spectroscopy.

Specific Synthetic Procedures

EXAMPLE 1A:

N,N-dimethyl-Val-Val-N-methyl-Val-Pro-Pro-Val-Phe-NH$_2$ 1.98 g of Fmoc-RINK-resin (substitution 0.46 mmol/g), corresponding to a batch size of 0.84 mmol, were reacted as in Ib above with 1.26 mmol each of Fmoc-Phe-OH Fmoc-Val-OH Fmoc-Pro-OH Fmoc-Pro-OH Fmoc-N-methyl-Val-OH Fmoc-Val-OH Fmoc-Val-OH The amino acid following the N-methyl amino acid was coupled on with PyBrop as coupling reagent. After the iterative synthetic cycles were completed, the peptide-resin underwent N-terminal deprotection (steps 2–4 in Ib), and was further reacted with aqueous formaldehyde solution as in II and then dried under reduced pressure. The resulting resin was subjected to TFA cleavage as in IV. The crude product (590 mg) was purified by gel filtration (SEPHADEX-LH-20). The yield was 295 mg.

EXAMPLE 1A:

Example 1 can also be prepared via classical solution phase methodology. The synthesis of N,N-dimethyl-Val-Val-N-methyl-Val-Pro-Pro-Val-Phe-NH$_2$ and its associated intermediates is described in the following paragraph.

a) Z-MeVal-Pro-OMe 66.25 g (250 mmol) of Z-MeVal-OH were dissolved in 250 ml of dry dichloromethane. After addition of 36.41 ml (262.5 mmol) of triethylamine, the reaction mixture was cooled to −25° C. and 32.37 ml (262.5 mmol) pivaloyl chloride were added. After stirring for 2.5 hours, 41.89 g (250 mmol) of H-Pro-OMe-HCl in 250 ml of dichloromethane, neutralized with 36.41 ml (262.5 mmol) triethylamine at 0° C., were added to the reaction mixture. Stirring was continued for 2 h at −25° C. and overnight at room temperature. The reaction mixture was diluted with dichloromethane and thoroughly washed with saturated aqueous NaHCO$_3$ solution (3×), water (1×), 5% citric acid (3×) and saturated NaCl solution. The organic phase was dried over sodium sulfate, filtered and evaporated to dryness. The residue (91.24 g) was stirred with petroleum ether overnight and filtered. 62.3 g of product were obtained.

b) H-MeVal-Pro-OMe 48.9 g (130 mmol) Z-MeVal-Pro-OMe were dissolved in 490 ml of methanol. After addition of 10.9 ml (130 mmol) concentrated hydrochloric acid and 2.43 g of 10% palladium/charcoal, the reaction mixture was hydrogenated. Filtration and evaporation to dryness yielded 36.43 g of product.

c) Z-Val-MeVal-Pro-OMe 18.1 g (65 mmol) of H-MeVal-Pro-OMe, 21.6 g (78 mmol) Z-Val-N-carboxyanhydride and 22.8 ml (130 mmol) diisopropylethylamine were stirred in 110 ml of DMF at 40° C. for 2 days. After evaporation of DMF, dichloromethane was added and the organic phase washed with saturated aqueous NaHCO$_3$ solution (3×), water (1×) 5% citric acid (3×) and saturated NaCl solution. The organic phase was dried over sodium sulfate, filtered and evaporated to dryness. The product (29.3 g) was obtained as a viscous oil.

d) H-Val-MeVal-Pro-OMe 29.3 g (61.6 mmol) of Z-Val-MeVal-Pro-OMe were dissolved in 230 ml of methanol. After addition of 1.15 g of 10% palladium/charcoal, the reaction mixture was hydrogenated. Filtration and evaporation to dryness yielded 21.96 g of product.

e) Z-Val-Val-MeVal-Pro-OMe 15.29 g (61 mmol) of Z-Val-OH and 21.96 g (61 mmol) of H-Val-MeVal-Pro-OMe were dissolved in 610 ml of dichloromethane and cooled to 0° C. After addition of 8.16 mol(73.2 mmol) of N-methylmorpholine, 2.77 g (20.3 mmol) of HOBt and 11.74 g (61 mmol) of EDCI, the reaction mixture was stirred overnight at room temperature, diluted with dichloromethane and thoroughly washed with saturated aqueous NaHCO$_3$ solution (3×), water (1×), 5% citric acid (3×) and saturated NaCl solution. The organic phase was dried over sodium sulfate, filtered and evaporated to dryness to yield 31.96 g of the product.

f) Z-Val-Val-MeVal-Pro-OH 31.96 g (57 mmol) of Z-Val-Val-MeVal-Pro-OMe were dissolved in 250 ml of methanol. 102.6 ml of a 1N LIOH solution was added and the mixture stirred overnight at room temperature. After addition of 500 ml of water, the aqueous phase was washed three times with ethyl acetate. The organic phase was dried over sodium sulfate, filtered and evaporated to dryness yielding 30.62 g of the desired product as a white solid.

g) Z-Val-Val-MeVal-Pro-Pro-Val-Phe-NH$_2$ 25 g (43.3 mmol) of Z-Val-Val-MeVal-Pro-OH and 15.59 g (43.3 mmol) of H-Pro-Val-Phe-NH$_2$ were suspended in 430 ml of dry dichloromethane. After cooling to 0° C., 5.81 ml (52 mmol) N-methylmorpholine, 1.97 g (15 mmol) of HOBt and 8.33 g (43.3 mmol) of EDCI were added and the reaction mixture stirred overnight at room temperature. The solvents were evaporated, the residue dissolved in 640 ml of dichloromethane and thoroughly washed with saturated aqueous NaHCO$_3$ solution (4×), water (1×), 5% citric acid (3×) and saturated NaCl solution. The organic phase was dried over sodium sulfate, filtered and evaporated to dryness to yield 33.04 g of the product. The crude product was chromatographed on a silica gel column with 20% MeOH/ hexane. 18.32 g of the desired product were obtained.

h) N,N-dimethyl-Val-Val-MeVal-Pro-Pro-Val-Phe-NH$_2$ 18.32 g of Z-Val-Val-MeVal-Pro-Pro-Val-Phe-NH$_2$ were dissolved in 80 ml of methanol. 0.4 g of 10% palladium/ carbon were added under nitrogen atmosphere and the reaction mixture hydrogenated at room temperature for 4 hours. After addition of 6.22 ml (81.24 mmol) of a 37% aqueous formaldehyde solution, hydrogenation was continued for 5 hours. Filtration and evaporation of the solvent gave rise to 15.6 g of crude product. Further purification was achieved by dissolving the peptide in water, adjusting the pH to 2 and extracting the aqueous phase three times with ethyl acetate. The aqueous phase was then adjusted to pH 8–9 and extracted four times with ethyl acetate. The organic phase was washed with water and dried over sodium sulfate, filtered and evaporated to yield 11.3 g of purified product as a white powder. The compound was characterized by fast atom bombardment mass spectrometry ([M+H]$^+$=797).

EXAMPLE 2A:

N,N-dimethyl-Val-Val-NMe-Val-Pro-{1-[thiazol-(2)-yl]-2-phenyl}-ethylamide 4.11 g of Fmoc-Pro-p-alkoxybenzyl-alcohol-resin (substitution 0.73 mmol/g), corresponding to a batch size of 3 mmol, were reacted as in Ib with 4.5 mmol each of Fmoc-N-MeVal-OH Fmoc-Val-OH Fmoc-Val-OH The amino acid following the N-methylamino acid was in this case reacted with double coupling using PyBrop or Bop-Cl with increased reaction times. After the synthesis was complete, the peptide-resin underwent N-terminal deprotection (Steps 2–4 in Ib), and was further reacted with aqueous formaldehyde solution as in II and then dried under reduced pressure. The resin obtained in this way was subjected to TFA cleavage as in IV. The crude product (750 mg) was employed directly for the next coupling. 100 mg of this compound were reacted with 45 mg of (S)-2-[1-amino-2-phenylethyl]thiazole and 230 mg of PyBop with the addition of 192 microliters of DIPEA in DMF at room temperature for 2 days. The reaction mixture was purified by gel chromatography (SEPHADEX LH-20, methanol) and the product fractions were combined. 83 mg of product were obtained.

EXAMPLE 1B

Me$_2$Val-Val-MeVal-Pro-Pro-NHCH(CH$_3$)$_2$ a) Z-MeVal-Pro-OMe 66.25 g (250 mmol) Z-MeVal-OH were dissolved in 250 ml dry dichloromethane. After addition of 36.41 ml (262.5 mmol) triethylamine, the reaction mixture was cooled to –25° C. and 32.27 ml (262.5 mmol) pivaloyl chloride were added. After stirring for 2.5 h, 41.89 g (250 mmol) H-Pro-OMe×HCl in 250 ml dichloromethane, neutralized with 36.41 ml (262.5 mmol) triethylamine at 0° C., were added to the reaction mixture. Stirring continued for 2 h at –25° C. and overnight at room temperature. The reaction mixture was diluted with dichloromethane and thoroughly washed with saturated aqueous NaHCO$_3$ solution (3×), water (1×), 5% citric acid (3×) and saturated NaCl solution. The organic phase was dried over sodium sulfate, filtered and evaporated to dryness. The residue (91.24 g) was stirred with petroleum ether overnight and filtered. 62.3 g of product were obtained.

b) H-MeVal-Pro-OMe 48.9 g (130 mmol) Z-MeVal-Pro-OMe were dissolved in 490 ml methanol. After addition of 10.9 ml (130 mmol) concentrated hydrochloric acid and 2.43 g 10% Palladium/charcoal, the reaction mixture was hydrogenated. Filtration and evaporation to dryness yielded 36.43 g of the product.

c) Z-Val-MeVal-Pro-OMe 18.1 g (65 mmol) H-MeVal-Pro-OMe, 21.6 g (78 mmol) Z-Val-N-carboxyanhydride and 22.8 ml (130 mmol) diisopropylethylamine were stirred in 110 ml DMF at 40° C. for 2 d. After evaporation of DMF, dichloromethane was added and the organic phase washed with saturated aqueous NaHCO$_3$ solution (3×), water (1×), 5% citric acid (3×) and saturated NaCl solution. The organic phase was dried over sodium sulfate and evaporated to dryness. The product (29.3 g) was obtained as a viscous oil.

d) H-Val-MeVal-Pro-OMe 29.3 g (61.6 mmol) of Z-Val-MeVal-Pro-OMe were dissolved in 230 ml methanol. After addition of 1.15 g 10% Palladium/charcoal, the reaction mixture was hydrogenated. Filtration and evaporation to dryness yielded 21.96 g of the product.

e) Z-Val-Val-MeVal-Pro-OMe 15.29 g (61 mmol) Z-Val-OH and 21.96 g (61 mmol) H-Val-MeVal-Pro-OMe were dissolved in 610 ml dichloromethane and cooled to 0° C. After addition of 8.16 ml (73.2 mmol) N-Methylmoropholine, 2.77 g (20.3 mmol) HOBt and 11.74 g (61 mmol) EDCI, the reaction mixture was stirred overnight at room temperature, diluted with dichloromethane and thoroughly washed with saturated aqueous NaHCO$_3$ solution (3×), water (1×), 5% citric acid (3×) and saturated NaCl solution. The organic phase was dried over sodium sulfate, filtered and evaporated to dryness to yield 31.96 g of the product.

f) Z-Val-Val-MeVal-Pro-OH 31.96 g (57 mmol) Z-Val-Val-MeVal-Pro-OMe were dissolved in 250 ml methanol. 102.6 ml of a 1 N LIOH solution was added and the mixture stirred overnight at room temperature. After addition of 500 ml water, the aqueous phase was washed three times with ethyl acetate, adjusted to pH 2 at 0° C. and extracted three times with ethyl acetate. The organic phase was dried over sodium sulfate, filtered and evaporated to dryness yielding 30.62 g of the desired product as a white solid.

g) Z-Val-Val-MeVal-Pro-Pro-NHCH(CH$_3$)$_2$ 2 g (3.35 mmol) Z-Val-Val-MeVal-Pro-OH and 0.664 g (3.35 mmol) H-Pro-NHCH(CH$_3$)$_2$ were dissolved in 34 ml of dry dichloromethane. After cooling to 0° C., 1.35 ml (12.1 mmol) N-methylmorpholine, 0.114 g (0.84 mmol) HOBt and 0.645 g (3.35 mmol) EDCI were added and the reaction mixture stirred overnight at room temperature. 80 ml dichloromethane were added and the organic phase thoroughly washed with saturated aqueous NaHCO$_3$ solution (3×), water (1×), 5% citric acid (3×) and saturated NaCl solution (1×). The organic phase was dried over sodium sulfate, filtered and evaporated to dryness to yield 1.96 g of the product which was used in the next reaction without further purification.

h) Me$_2$Val-Val-MeVal-Pro-Pro-NHCH(CH$_3$)$_2$ 1.96 g Z-Val-Val-MeVal-Pro-Pro-NHCH(CH$_3$)$_2$ were dissolved in 11 ml methanol. 0.054 g 10% Pd/C were added under nitrogen atmosphere and the reaction mixture hydrogenated at room temperature for 4 h. After addition of 0.86 ml (11.24 mmol) of a 37% aqueous formaldehyde solution and 0.281 g 10% Pd/C, hydrogenation was continued for 5 h. Filtration and evaporation of the solvent gave rise to 2.77 g of crude product. Further purification was achieved by dissolving the peptide in water, adjusting the pH to 2 and extracting the aqueous phase three times with ethyl acetate. The aqueous phase was then adjusted to pH 8–9 and extracted four times with dichloromethane. The organic phase was dried over sodium sulfate, filtered and evaporated to yield 1.37 g of purified product as a white foam. The compound was further purified using medium pressure liquid chromatography (10–50% A in 10 min.; 50–90% A in 320 min.). Fractions containing the product were combined, lyophilized, redissolved in water and the pH adjusted to 9 with 1 N LiOH. After extraction with dichloromethane, the organic phase was dried over sodium sulfate, filtered and evaporated to dryness. Lyophilization led to 500 mg of pure product, which was characterized by fast atom bombardment mass spectrometry ([M+H]$^+$=593).

EXAMPLE 2B

Me$_2$Val-Val-MeVal-Pro-Pro-NHC(CH$_3$)$_3$ a) Z-Val-Val-MeVal-Pro-Pro-NHC(CH$_3$)$_3$ 2 g (3.35 mmol) Z-Val-Val-MeVal-Pro-OH and 0.692 g (3.35 mmol) H-Pro-NHC(CH$_3$)$_3$ were dissolved in 34 ml of dry dichloromethane. After cooling to 0° C., 1.35 ml (12.1 mmol) N-methylmorpholine, 0.114 g (0.84 mmol) HOBt and 0.645 g (3.35 mmol) EDCI were added and the reaction mixture stirred overnight at room temperature. 80 ml dichloromethane were added and the organic phase thoroughly washed with saturated aqueous NaHCO$_3$ solution (3×), water (1×), 5% citric acid (3×) and saturated NaCl solution (1×). The organic phase was dried over sodium sulfate, filtered and evaporated to dryness to yield 1.8 g of the product which was used in the next reaction without further purification.

b) Me$_2$Val-Val-MeVal-Pro-Pro-NHC(CH$_3$)$_3$ 1.8 g Z-Val-Val-MeVal-Pro-Pro-NHC(CH$_3$)$_3$ were dissolved in 10 ml methanol. 0.045 g 10% Pd/C were added under nitrogen atmosphere and the reaction mixture hydrogenated at room temperature for 4 h. After addition of 0.86 ml (11.24 mmol) of a 37% aqueous formaldehyde solution and 0.252 g 10% Pd/C, hydrogenation was continued for 5 h. Filtration and evaporation of the solvent gave rise to 1.82 g of crude product. The compound was further purified using medium pressure liquid chromatography (10–50% A in 10 min.; 50–90% A in 320 min.). Fractions containing the product were combined, lyophilized, redissolved in water and the pH adjusted to 9 with 1 N LiOH. After extraction with dichloromethane, the organic phase was dried over sodium sulfate and evaporated to dryness. Lyophilization led to 547 mg of pure product, which was characterized by fast atom bombardment mass spectrometry ([M+H]$^+$=607).

Evaluation of Biological Activity

In vivo Methodology

The Dolastatin-15 derivative of Formula I, designated compound ii in FIG. 1A, was tested using a standard animal model for rheumatoid arthritis known as Collagen induced arthritis (CIA) (See, e.g., Banerjee, et al., *The Journal of Immunology* 142: 2237–2243 (1989) ). CIA is a useful animal model of rheumatoid arthritis that serves as an in vivo system for the exploration of inflammatory synovitis etiologies and for the investigation of potentially new therapeutic interventions. Other suitable models can also be used in this invention.

Collagen induced arthritis in mice in induced by intradermal injection of chick collagen type II emulsified in complete Freund's adjuvant, with the onset of symptoms typically occurring on or around day 26 post immunization.

In general, any dosing regimen which appears to provide an acceptable level of suppression of rheumatoid arthritis is suitable. Any acceptable method of drug administration can be determined using techniques well known to those of skill in the art. In addition, the Dolastatin-15 derivatives of Formula I can be administered in combination with other drugs known to be useful in the treatment of rheumatoid arthritis, as described earlier.

EXAMPLE 3

Collagen Induced Arthritis—Prophylactic Model

DBA-1 mice, which is a strain of mouse susceptible to collagen induced arthritis, were used in all experiments (See e.g., The *FASEB*, 2 :2950 (1988)). Mice were immunized intradermally on day 0 with 100 μg of chick collagen type II in complete Freud's adjuvant.

Three treatment groups were evaluated and consisted of saline treated animals (control), dexamethasone treated animals (standard therapy), and compound ii treated animals. Treatment was commenced for all groups on day 26 post immunization just prior to the onset of symptoms and was ended on day 35 post immunization. Dexamethasone was injected intraperitoneally at a dose of 5 mg/kg/day, compound ii was given orally, by gavage, at a dose of 50 mg/kg/day using saline as the vehicle and saline was administered orally once a day as a control.

Mean Arthritic Score

The degree of arthritis severity was recorded by daily observation of each paw. An integer scale of 0–5 was used to quantify the level of erythema, swelling, deformity and joint stiffness in each paw with 0=normal and 5=maximum. The sum of all four paws represents the mean arthritic score, with a score of 20 being the maximum. The results are depicted graphically in FIG. 2.

The results show that none of the animals treated with compound ii had signs of rheumatoid arthritis up to 6 days after the end of treatment. The dexamethasone treated animals, however, exhibited signs of rheumatoid arthritis immediately following the end of treatment.

EXAMPLE 4

Collagen Induced Arthritis—Therapeutic Model

DBA-1 mice were used in all experiments. Mice were immunized intradermally on day 0 with 100 μg of chick collagen type II. Symptom onset occurred around day 35 post immunization Three treatment groups were evaluated and consisted of vehicle treated animals (control), dexamethasone treated animals (standard therapy), and compound ii treated animals. Treatment was commenced for all groups on day 48 post immunization, when the arthritic score of all animals had reached 3–4. The mean arthritic scores of mice in the three groups were equivalent at the start of treatment. Animals were treated for 21 days. Dexamethasone was injected intraperitoneally at a dose of 5 mg/kg/day, compound ii was given orally by gavage at a dose of 50 mg/kg/day using saline as a vehicle and vehicle alone was administered by gavage (0.25 ml) as control.

Mean Arthritic Score

The degree of arthritis severity was recorded by daily scoring of each paw. An integer scale of 0–5 was used to quantify the level of erythema, swelling, deformity and joint stiffness with 0=normal and 5=maximum. The sum of all four paws represents the mean arthritic score with a score of 20 being the maximum. The results are depicted graphically in FIG. 3.

The results show that animals treated with compound ii showed a significant decrease in mean arthritic score as compared to control (P Value less than 0.01–0.05, as determined by the Mann-Whitney Test).

Histopathological Results

Figure 4:
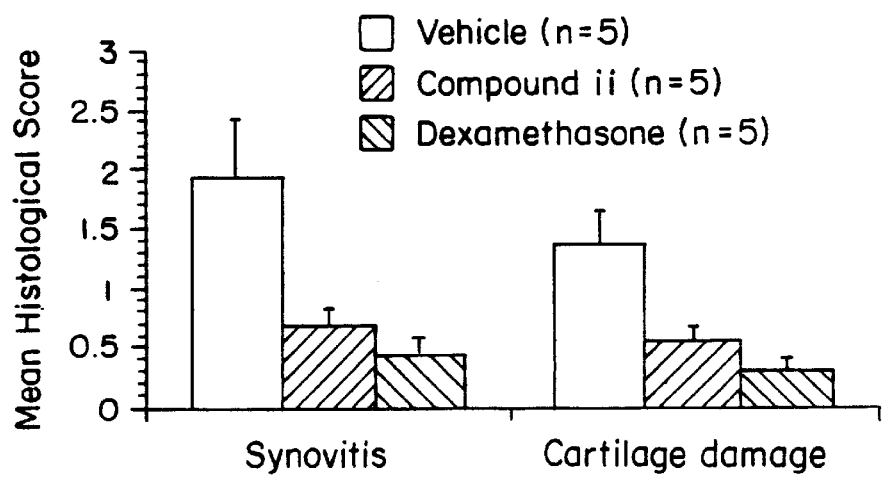
FIG. 4 is a graph showing the degree of synovitis and cartilage damage as determined by histopathological analysis for mice treated with vehicle, dexamethasone (standard therapy) and compound ii of FIG. 1A. The mice were treated starting at 48 days after immunization with type II collagen and treatment lasted for 21 days. Necropsy was conducted on day 71 post-immunization.

Five mice from each treatment group were necropsied on day 71 post immunization and histopathology was performed on the joints from all four paws from each mouse. Both synovial inflammation and cartilage damage of affected joints were graded on a scale from 0–3. Results are shown in FIG. 4. Treatment with compound ii and dexamethasone significantly suppressed synovitis and cartilage involvement as compared to the vehicle treated animals. The following compounds were prepared and can be prepared according to the Examples:

3. Xaa Val Xab Pro Xac
4. Xaa Val Xab Pro Xad
5. Xaa Val Xab Pro Xae
6. Xaa Val Xab Pro Xaf
7. Xaa Val Xab Pro Xag
8. Xaa Val Xab Pro Xah
9. Xaa Val Xab Pro Xai
10. Xaa Val Xab Pro Xak
11. Xaa Val Xab Pro Xal
12. Xaa Val Xab Pro Xam
13. Xaa Val Xab Pro Xan
14. Xaa Val Xab Pro Xao
15. Xaa Val Xab Pro Xap
16. Xaa Val Xab Pro Xaq
17. Xaa Val Xab Pro Xar
18. Xaa Val Xab Pro Xas
19. Xaa Val Xab Pro Xat
20. Xaa Val Xab Pro Xau
21. Xaa Val Xab Pro Xav
22. Xaa Val Xab Pro Xaw
23. Xaa Val Xab Pro Xax
24. Xaa Val Xab Pro Xay
25. Xaa Val Xab Pro Xaz
26. Xaa Val Xab Pro Xba
27. Xaa Val Xab Pro Xbb
28. Xaa Val Xbc Pro Xay
29. Xaa Val Xab Pro Xbd
30. Xaa Val Xab Pro Xbe
31. Xaa Val Xab Pro Xbf
32. Xaa Val Xab Pro Xbg
33. Xaa Val Xab Pro Xbh
34. Xaa Val Xab Pro Xbi
35. Xaa Val Xab Pro Xbk
36. Xaa Val Xab Pro Xbl
37. Xaa Val Xab Pro Xbm
38. Xaa Val Xab Pro Xbn
39. Xaa Val Xab Pro Xbo
40. Xaa Val Xab Pro Xbp
41. Xaa Val Xab Pro Xbq
42. Xaa Val Xab Pro Xbr
43. Xaa Val Xab Pro Xbs
44. Xaa Val Xab Pro Xbt
45. Xaa Val Xab Pro Xbu
46. Xaa Val Xab Pro Xbv
47. Xaa Val Xab Pro Xbw
48. Xaa Val Xab Pro Xbx
49. Xaa Val Xab Pro Xby
50. Xaa Val Xab Pro Xbz
51. Xaa Val Xab Pro Xca
52. Xaa Val Xab Pro Xcb
53. Xaa Val Xab Pro Xcc
54. Xaa Val Xab Pro Xcd
55. Xaa Val Xab Pro Xce
56. Xaa Val Xab Pro Xcf
57. Xaa Xdf Xab Pro Xay
58. Xaa Val Xab Pro Xch
59. Xaa Val Xab Pro Xci
60. Xaa Val Xab Pro Xck
61. Xaa Val Xab Pro Xcl
62. Xaa Val Xab Pro Xcm
63. Xaa Val Xab Pro Xcn
64. Xaa Val Xab Pro Xco
65. Xaa Val Xab Pro Xcp
66. Xaa Val Xab Pro Xcq
67. Xaa Val Xab Pro Xcr
68. Xaa Val Xab Pro Xcs
69. Xaa Val Xab Pro Xct

70. Xaa Val Xab Pro Xcu
71. Xcw Val Xab Pro Xcv
72. Xcx Val Xab Pro Xcv
73. Xaa Val Xab Pro Pro Xcy
74. Xaa Val Xab Pro Pro Xcz
75. Xaa Val Xda Pro Xcv
76. Xaa Xdb Xab Pro Xcv
77. Xdc Val Xab Pro Xcv
78. Xaa Ile Xab Pro Xcv
79. Xdd Val Xab Pro Xcv
80. Xde Val Xab Pro Xcv
81. Xaa Xdf Xab Pro Xcv
82. Xaa Val Xab Pro Xcg
83. Xaa Val Xab Pro Pro Xdg
84. Xaa Val Xab Pro Pro Xdh
85. Xaa Val Xab Pro Pro Xdi
86. Xaa Val Xab Pro Pro Xdk
87. Xaa Val Xdl Pro Xcv
88. Xde Val Xab Pro Xay
89. Xaa Val Xdl Pro Xay
90. Xaa Val Xab Pro Xdm
91. Xaa Val Xab Pro Xdn
92. Xaa Val Xab Pro Xdo
93. Xaa Val Xab Pro Xdp
94. Xaa Val Xab Pro Xdq
95. Xaa Val Xab Pro Pro Xdr
96. Xaa Val Xab Pro Xds
97. Xaa Val Xbc Pro Xcv
98. Xaa Ile Xab Pro Xay
99. Xcw Val Xab Pro Xay
100. Xaa Val Xbc Pro Xal
101. Xaa Val Xdl Pro Xal
102. Xaa Xdf Xab Pro Xal
103. Xaa Ile Xab Pro Xal
104. Xdd Val Xab Pro Xal
105. Xde Val Xab Pro Xal
106. Xcx Val Xab Pro Xcy
107. Xcw Val Xab Pro Xal
108. Xcx Val Xab Pro Xal
109. Xcw Val Xab Pro Xav
110. Xcx Val Xab Pro Xav
111. Xcw Val Xab Pro Xaw
112. Xcx Val Xab Pro Xaw
113. Xab Val Xab Pro Xay
114. Xab Val Xab Pro Xcv
115. Xab Val Xab Pro Xal
116. Xab Val Xab Pro Xam
117. Xab Val Xab Pro Xan
118. Xab Val Xab Pro Xao
119. Xab Val Xab Pro Xav
120. Xab Val Xab Pro Xaw
121. Xab Val Xab Pro Xat
122. Xab Val Xab Pro Xau
123. Xab Val Xab Pro Xbf
124. Xab Val Xab Pro Xbm
125. Xab Val Xab Pro Xbn
126. Xab Val Xab Pro Xbo
127. Xab Val Xab Pro Xch
128. Xaa Val Xab Pro Xdt
129. Xaa Val Xab Pro Xdu
130. Xaa Val Xab Pro Xdv
131. Xaa Val Xab Pro Xdw
132. Xaa Val Xab Pro Xdx
133. Xaa Val Xab Pro Xdy
134. Xaa Val Xab Pro Xdz
135. Xaa Val Xab Pro Xea
136. Xaa Val Xab Pro Xeb

137. Xaa Val Xab Pro Xec
138. Xaa Val Xab Pro Xed
139. Xaa Val Xab Pro Xef
140. Xaa Val Xab Pro Xeg
141. Xaa Val Xab Pro Xeh
142. Xaa Val Xab Pro Xei
143. Xaa Val Xab Pro Xek
144. Xaa Val Xab Pro Xel
145. Xaa Val Xab Pro Xem
146. Xaa Val Xab Pro Xen
147. Xaa Val Xab Pro Xeo
148. Xaa Val Xab Pro Xep
149. Xaa Val Xab Pro Xeq
150. Xaa Val Xab Pro Xer
151. Xaa Val Xab Pro Xcq
152. Xaa Val Xab Pro Pro Val Phe
153. Xaa Val Xab Pro Xet Val Phe NH$_2$
154. Xaa Val Xer Pro Pro Val Phe NH$_2$
155. Xaa Val Xbc Pro Pro Val Phe NH$_2$
156. Xaa Ile Xab Pro Pro Val Phe NH$_2$
157. Xaa Leu Xab Pro Pro Val Phe NH$_2$
158. Xde Val Xab Pro Pro Val Phe NH$_2$
159. Xdd Val Xab Pro Pro Val Phe NH$_2$
160. Xes Val Xab Pro Pro Val Phe NH$_2$
161. Xeu Val Xab Pro Pro Val Phe NH$_2$
162. Xaa Val Xab Pro Pro Phe Phe NH$_2$
163. Xaa Val Xab Pro Pro Val NH$_2$
164. Xaa Val Xab Pro Xev
165. Xaa Val Xab Pro Pro NH$_2$
166. Xaa Val Xab Pro Pro
167. Xaa Val Xab Pro Xew
168. Xaa Val Xab Xex
169. Xdd Val Xab Pro Pro NH$_2$
170. Xaa Xdf Xab Pro Pro NH$_2$
171. Xaa Val Xab Pro Xey
172. Xaa Val Xab Pro Xez
173. Xfa Val Xab Pro Pro Val Phe NH$_2$
174. Xaa Val Xab Pro Pro Xfb
175. Xaa Val Xab Pro Xfc
176. Xaa Val Xab Pro Xfd
177. Xaa Val Xab Pro Xfe
178. Xaa Val Xab Pro Xff
179. Xaa Val Xab Pro Xfg
180. Xaa Val Xab Pro Xfh
181. Xaa Val Xab Pro Xfi
182. Xaa Val Xab Pro Xfj
183. Xaa Val Xdl Pro Pro NH$_2$
184. Xaa Val Xfk Pro Pro NH$_2$
185. Xaa Val Xfl Pro Xfh
186. Xaa Val Xfk Pro Xfh
187. Xcx Val Xab Pro Xfh
188. Xaa Val Xab Pro Pro Xdf Phe NH$_2$
189. Xaa Val Xab Pro Pro Leu Phe NH$_2$
190. Xaa Val Xab Pro Pro Ile Phe NH$_2$

TABLE

SEQUENCE IDENTIFICATION OF COMPOUNDS PREPARED ACCORDING TO THE EXAMPLES AND CONTAINED IN THE FIGURE

| Compound Number(s) | SEQ ID NO: |
|---|---|
| 2A, 3–56, 58–72, 75, 77, 79–80, 82, 87–94, 96–97, 99–101, 104–151, 164, 167, 171–172, 175–182, 185–187, and Compounds i-xvii of the Figure | 1 |
| 57 | 2 |
| 73–74, 83–86, 95, 174 | 3 |
| 76, 81, 102 | 4 |
| 78, 98, 103 | 5 |
| 1A, 152, 154–155, 158–161, 173 | 6 |
| 153 | 7 |
| 156 | 8 |
| 157 | 9 |
| 162 | 10 |
| 163 | 11 |
| 1B, 2B, 165–166, 169, 183 | 12 |
| 168 | 13 |
| 170 | 14 |
| 188 | 15 |
| 189 | 16 |
| 190 | 17 |

Examples for the MS-characterization of the synthesized novel compounds are listed below:

| EXAMPLE analysis | Fast atom bombardment MS |
|---|---|
| 3. | 565 |
| 4. | 579 |
| 5. | 593 |
| 6. | 607 |
| 7. | 621 |
| 8. | 635 |
| 11. | 607 |
| 12. | 607 |
| 13. | 621 |
| 14. | 649 |
| 15. | 635 |
| 16. | 635 |
| 17. | 635 |
| 18. | 635 |
| 19. | 621 |
| 20. | 621 |
| 21. | 635 |
| 22. | 635 |
| 25. | 633 |
| 26. | 647 |
| 27. | 661 |
| 31. | 623 |
| 32. | 671 |
| 33. | 667 |
| 34. | 681 |
| 35. | 655 |
| 36. | 655 |
| 37. | 669 |
| 38. | 621 |
| 39. | 635 |
| 41. | 649 |
| 42. | 621 |
| 43. | 633 |
| 44. | 667 |
| 45. | 607 |
| 46. | 647 |
| 47. | 668 |
| 48. | 655 |
| 49. | 669 |
| 50. | 685 |
| 51. | 629 |
| 52. | 625 |
| 53. | 721 |
| 55. | 579 |
| 58. | 623 |
| 61. | 597 |
| 62. | 621 |
| 63. | 609 |
| 64. | 625 |
| 65. | 635 |
| 66. | 591 |

-continued
| EXAMPLE analysis | Fast atom bombardment MS |
|---|---|
| 67. | 715 |
| 68. | 685 |
| 69. | 685 |
| 70. | 591 |
| 71. | 607 |
| 72. | 621 |
| 74. | 706 |
| 75. | 579 |
| 76. | 579 |
| 77. | 579 |
| 78. | 607 |
| 79. | 607 |
| 80. | 607 |
| 81. | 607 |
| 82. | 637 |
| 83. | 692 |
| 84. | 706 |
| 85. | 706 |
| 86. | 706 |
| 87. | 607 |
| 90. | 635 |
| 92. | 659 |
| 93. | 617 |
| 94. | 636 |
| 95. | 678 |
| 128. | 671 |
| 131. | 625 |
| 139. | 625 |
| 151. | 637 |
| 152. | 798 |
| 153. | 810 |
| 154. | 812 |
| 155. | 812 |
| 156. | 812 |
| 157. | 812 |
| 258. | 812 |
| 159. | 811 |
| 160. | 825 |
| 161. | 881 |
| 162. | 845 |
| 163. | 649 |
| 164. | 737 |
| 165. | 550 |
| 166. | 551 |
| 167. | 731 |
| 168. | 550 |
| 169. | 566 |
| 170. | 566 |
| 171. | 635 |
| 172. | 704 |
| 173. | 853 |
| 174. | 740 |
| 175. | 619 |
| 176. | 845 |
| 177. | 649 |
| 178. | 691 |
| 179. | 717 |
| 180. | 641 |
| 181. | 579 |
| 182. | 595 |
| 183. | 566 |
| 184. | 566 |
| 185. | 669 |
| 186. | 656 |
| 187. | 669 |
| 188. | 811 |
| 189. | 812 |
| 190. | 812 |
The symbols used in the description of the compounds of Formula I have the following meanings:
Xaa: N,N-Dimethylvaline
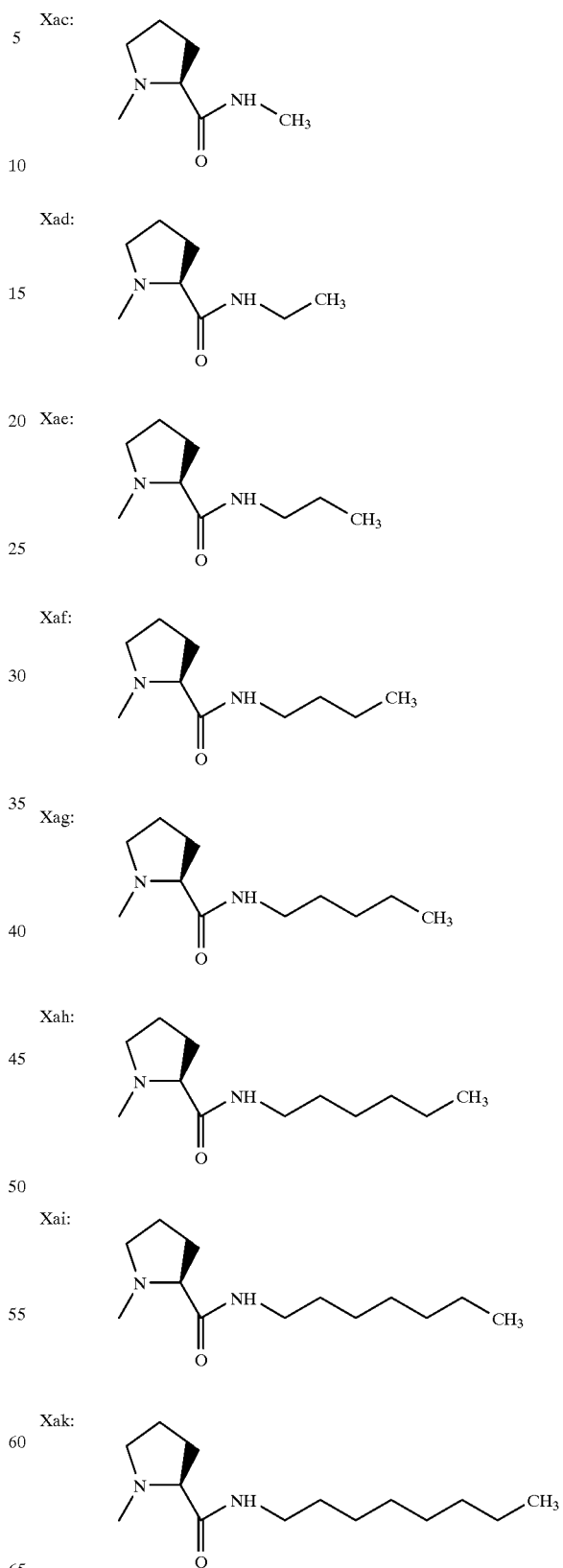
Xab: N-Methylvaline
Xac:
Xad:
Xae:
Xaf:
Xag:
Xah:
Xai:
Xak:

Xal: 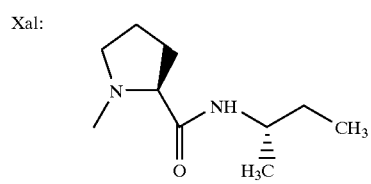
Xam: 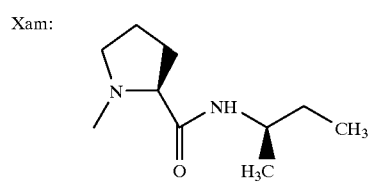
Xan: 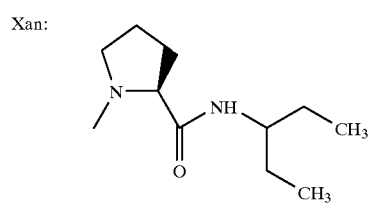
Xao: 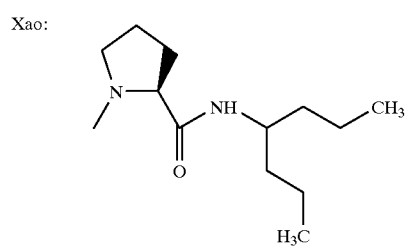
Xap: 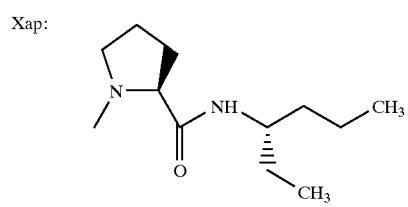
Xaq: 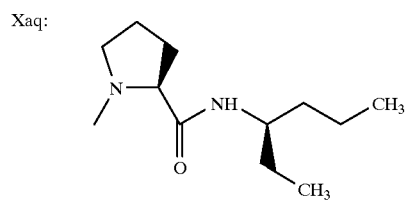
Xar: 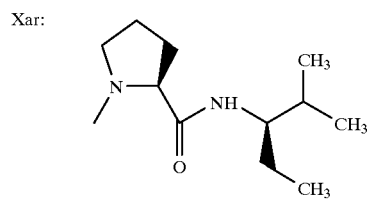
Xas: 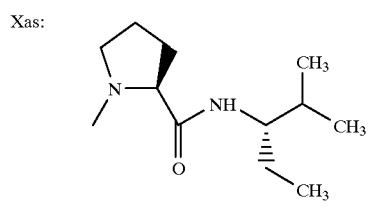
Xat: 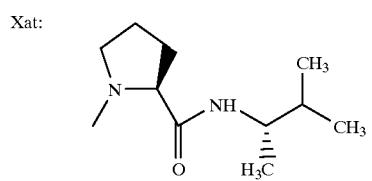
Xau: 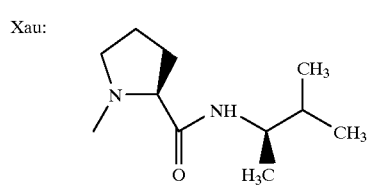
Xav: 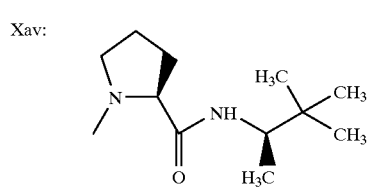
Xaw: 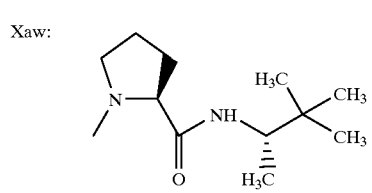
Xax: 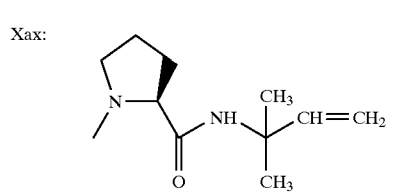
Xay: 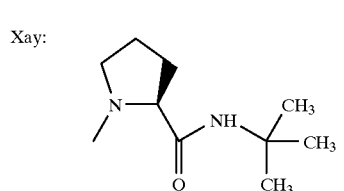
Xaz: 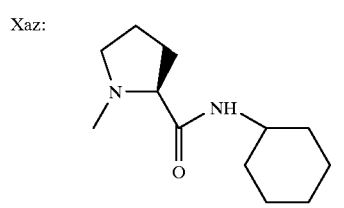

| | |
|---|---|
| Xba: | 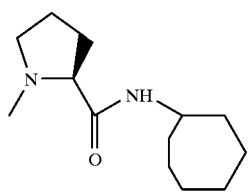 |
| Xbb: | 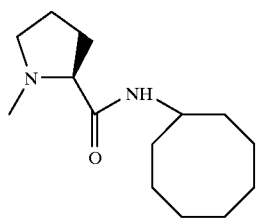 |
| Xbc: | N-Methyl-isoeucine |
| Xbd: | 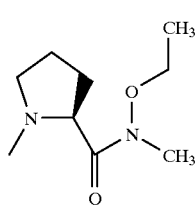 |
| Xbe: | 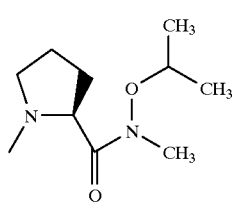 |
| Xbf: | 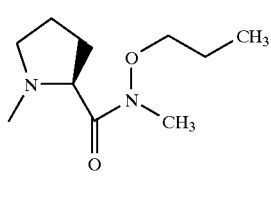 |
| Xbg: | 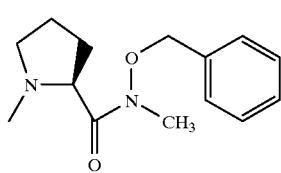 |
| Xbh: | 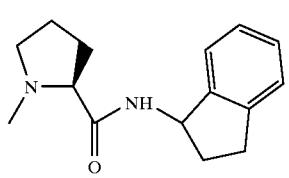 |
| Xbi: | 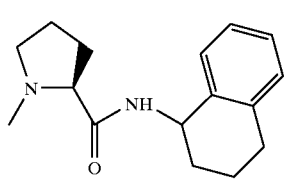 |
| Xbk: | 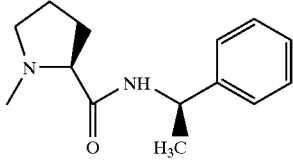 |
| Xbl: | 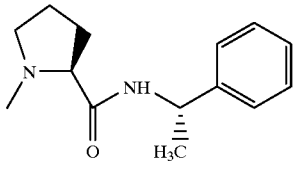 |
| Xbm: | 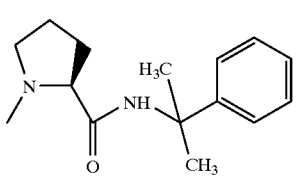 |
| Xbn: | 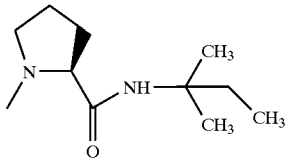 |
| Xbo: | 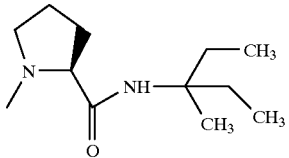 |
| Xbp: | 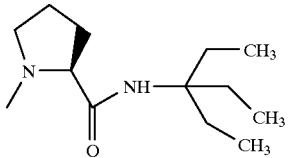 |
| Xbq: | 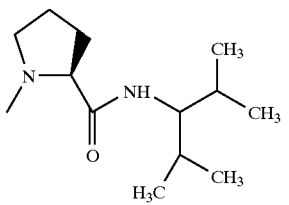 |
| Xbr: | 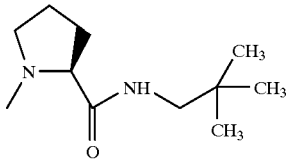 |

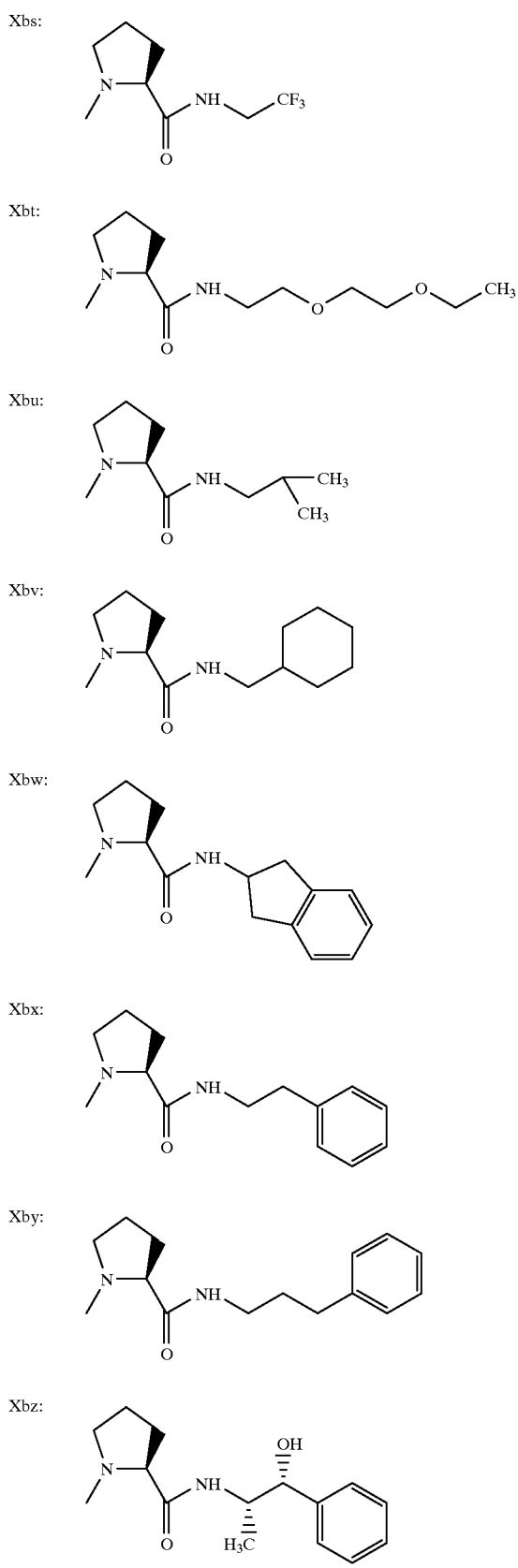
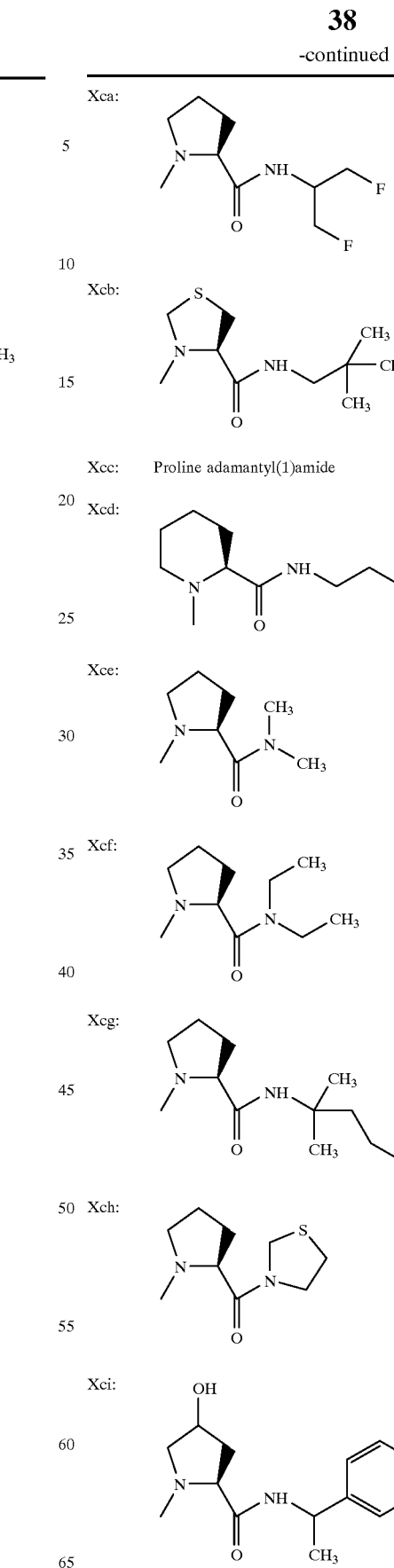

Xck: 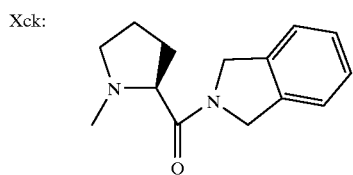
Xcl: 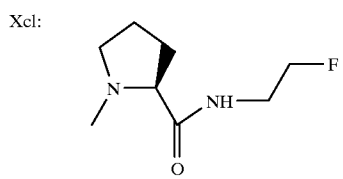
Xcm: 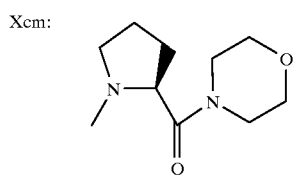
Xcn: 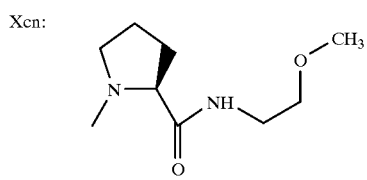
Xco: 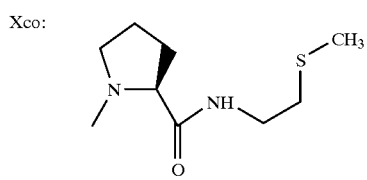
Xcp: 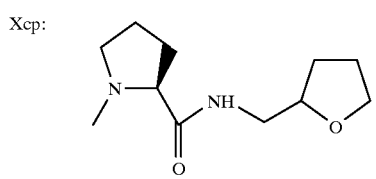
Xcq: 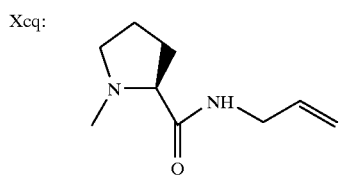
Xcr: 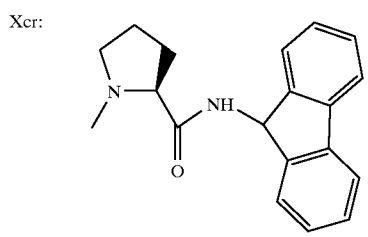
Xcs: 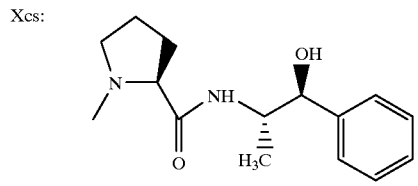
Xct: 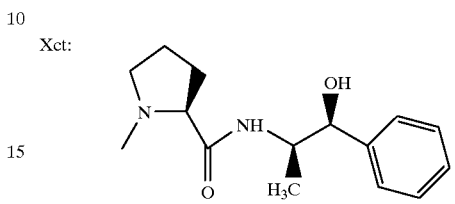
Xcu: 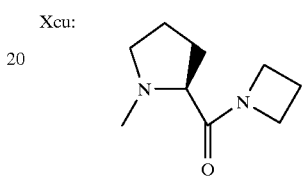
Xcv: 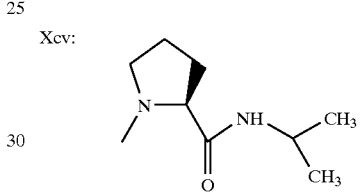
Xcw: N-Methyl-N-ethyl-valine
Xcx: N,N-Diethylvaline
Xcy: 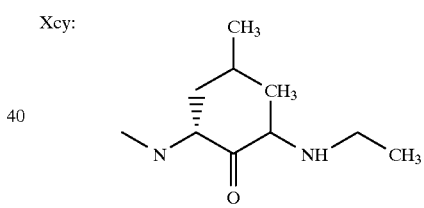
Xcz: 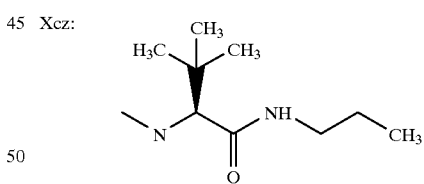
Xda: N-Methyl-2-aminobutyroyl
Xdb: 2-aminobutyroyl
Xdc: N,N-Dimethyl-2-aminobutyroyl
Xdd: N,N-Dimethyl-2-tert.butylglycine
Xde: N,N-Dimethyl-isoleucine
Xdf: 2-tert.butylglycine
Xdg: 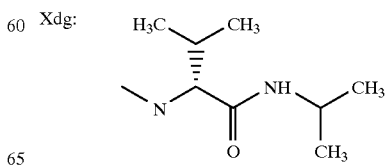

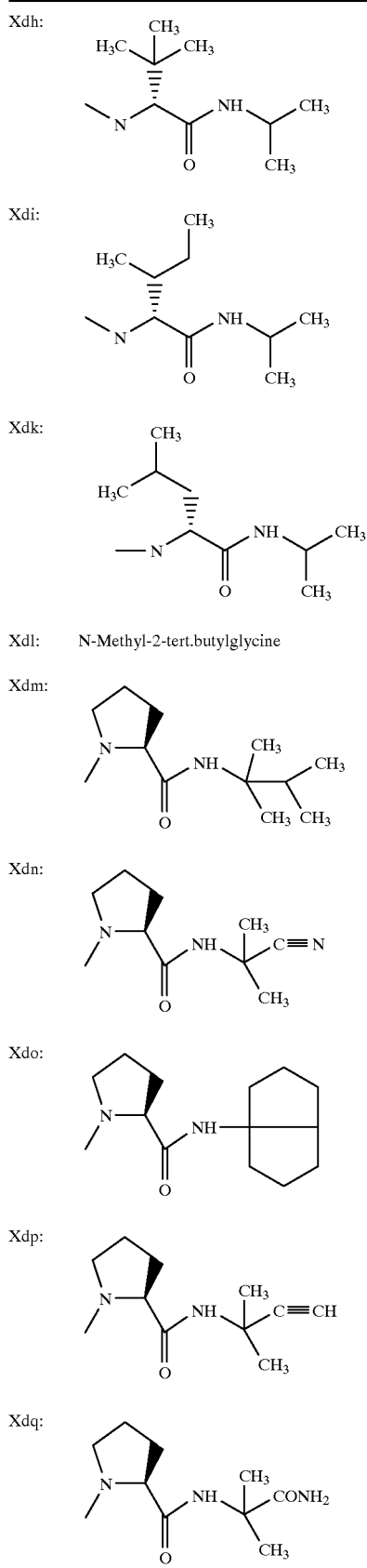
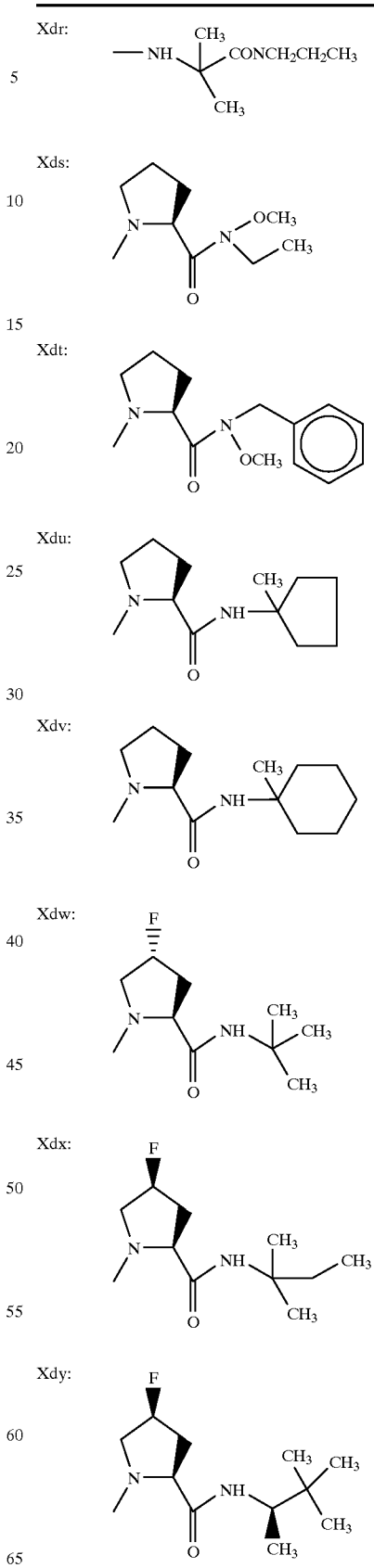
Xdl: N-Methyl-2-tert.butylglycine

Xdz: 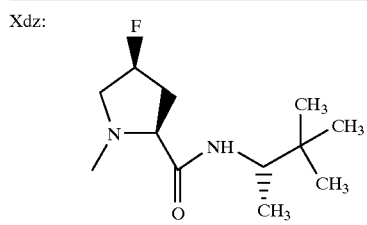
Xea: 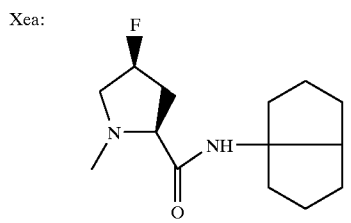
Xeb: 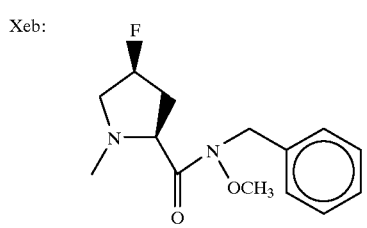
Xec: 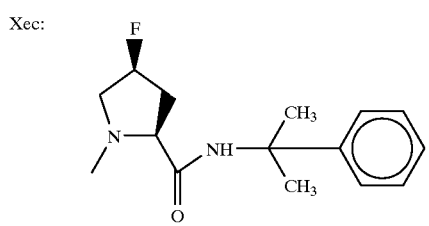
Xed: 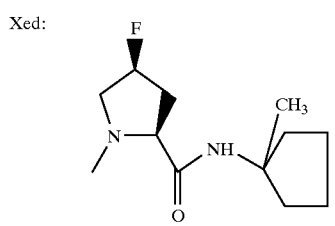
Xee: 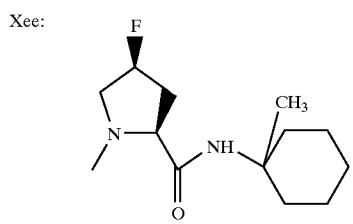
Xef: 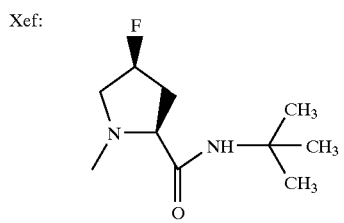
Xeg: 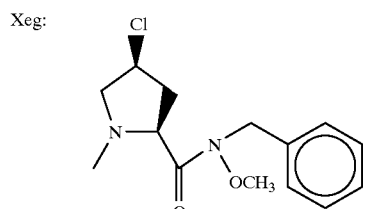
Xeh: 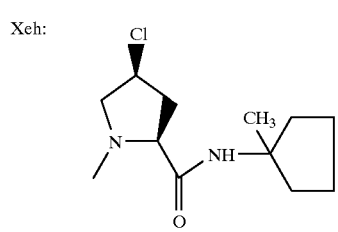
Xei: 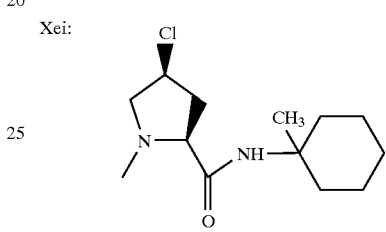
Xek: 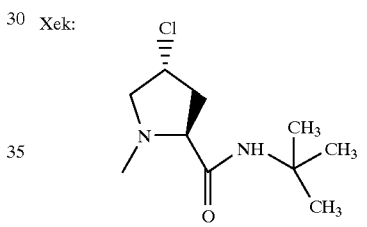
Xel: 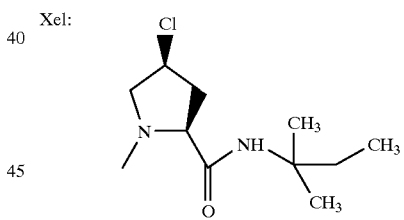
Xem: 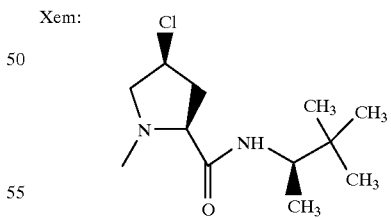
Xen: 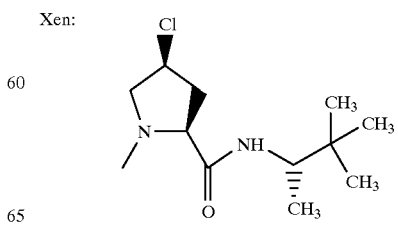

-continued
Xeo: 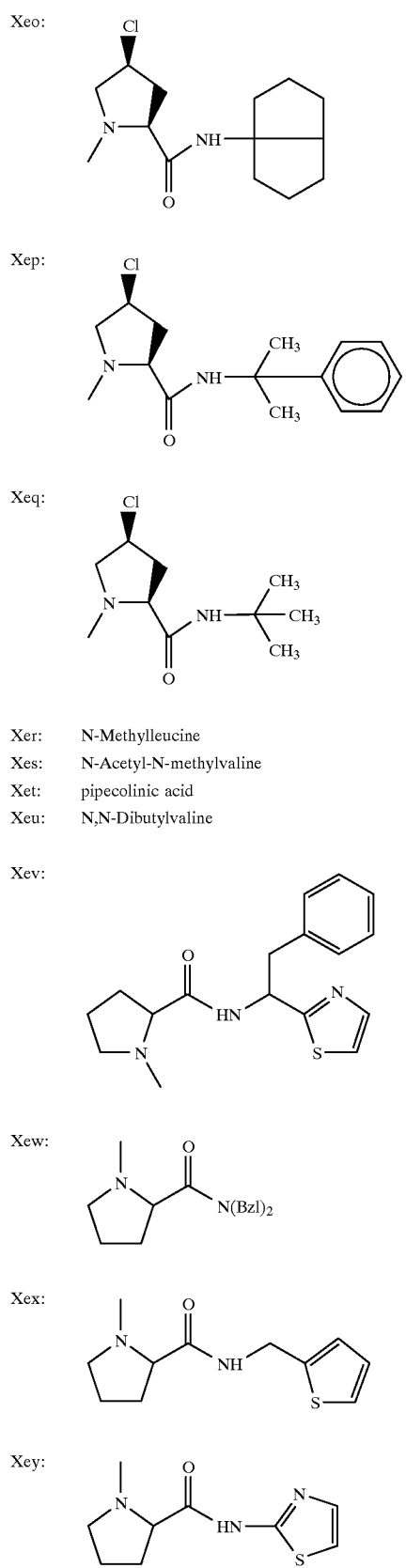
Xep:
Xeq:
Xer: N-Methylleucine
Xes: N-Acetyl-N-methylvaline
Xet: pipecolinic acid
Xeu: N,N-Dibutylvaline
Xev:
Xew:
Xex:
Xey:
-continued
Xez: 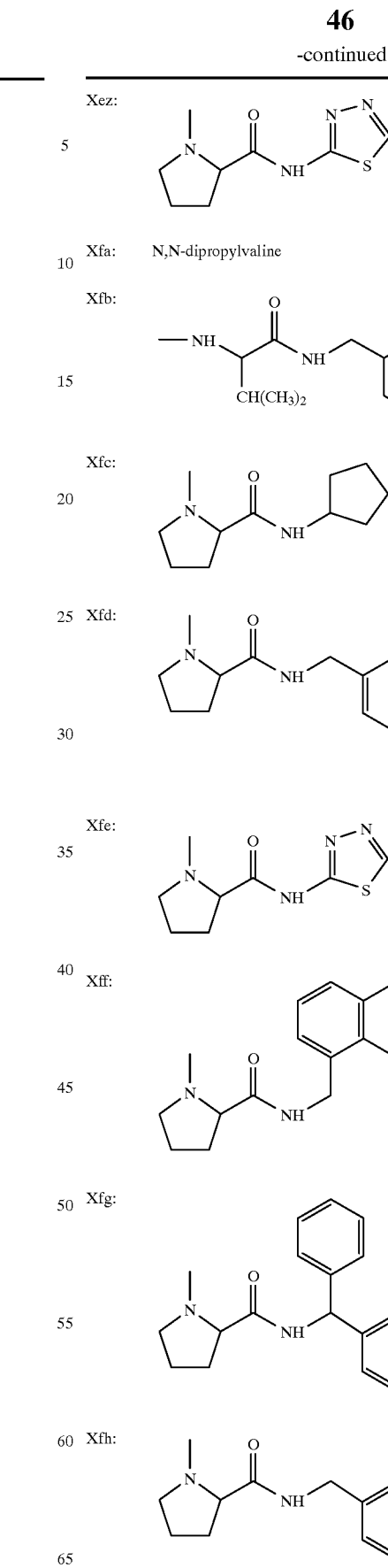
Xfa: N,N-dipropylvaline
Xfb:
Xfc:
Xfd:
Xfe:
Xff:
Xfg:
Xfh:

Xfi: 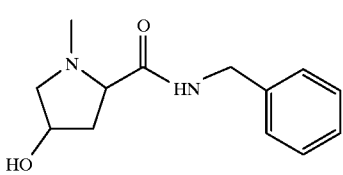

Xfj: 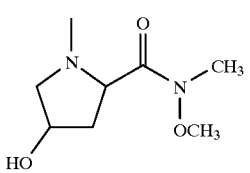

| | |
|---|---|
| Xfk: | N-Ethylvaline |
| Xfl: | N-Methyl-3-tert-butylalanine |

Equivalents

Those skilled in the art will recognize or be able to ascertain using no more than routine experimentation many equivalents to the specific embodiments of the invention described herein. Such equivalents are intended to be encompassed in the scope of the following claims.

What is claimed is:

1. A method for the treatment of rheumatoid arthritis in a mammal, comprising administering to said mammal a therapeutically effective amount of a compound of Formula I:

$$R^1R^2N-CHX-CO-A-B-D-(E)_s-(F)_t-(G)_u-K \quad (I)$$

wherein:
    $R^1$ is alkyl, cycloalkyl, alkylsulfonyl, fluoroalkyl, or aminosulfonyl;
    $R^2$ is hydrogen, alkyl, fluoroalkyl or cycloalkyl;
    $R^1-N-R^2$ together may be a pyrrolidino or piperidino residue;
    A is a valyl, isoleucyl, leucyl, allo-isoleucyl, 2,2-dimethylglycyl, 2-cyclopropylglycyl, 2-cyclopentylglycyl, 3-tert-butylalanyl, 2-tert-butylglycyl, 3-cyclohexylalanyl, 2-ethylglycyl, 2-cyclohexylglycyl, norleucyl or norvalyl residue;
    B is a N-alkyl-valyl, -norvalyl, -leucyl, -isoleucyl, -2-tert-butylglycyl, -3-tert-butylalanyl, -2-ethylglycyl, -2-cyclopropylglycyl, -2-cyclopentylglycyl, -norleucyl or -2-cyclohexylglycyl residue;
    D is a prolyl, homoprolyl, hydroxyprolyl, 3,4-dehydroprolyl, 4-fluoroprolyl, 3-methylprolyl, 4-methylprolyl, 5-methylprolyl, azetidine-2-carbonyl, 3,3-dimethylprolyl, 4,4-difluoroprolyl, oxazolidine-4-carbonyl or thiazolidine-4-carbonyl residue;

E is a prolyl, homoprolyl, hydroxyprolyl, 3,4-dehydroprolyl, 4-fluoroprolyl, 3-methylprolyl, 4-methyl prolyl, 5-methylprolyl, azetidine-2-carbonyl, 3,3-dimethylprolyl, 4,4-difluoroprolyl, oxazolidine-4-carbonyl or thiazolidine-4-carbonyl residue;

F and G are independently selected from the group consisting of prolyl, homoprolyl, hydroxyprolyl, thiazolidinyl-4-carbonyl, 1-aminopentyl-1-carbonyl, valyl, 2-tert-butylglycyl, isoleucyl, leucyl, 3-cyclohexylalanyl, phenylalanyl, N-methylphenylalanyl, tetrahydrosioquinolyl-2-histidyl, 1-aminoindyl-1-carbonyl, 3-pyridylalanyl, 2-cyclohexylglycyl, norleucyl, norvalyl, neopentylglycyl, trytophanyl, glycyl, 2,2-dimethylglycyl, alanyl, β-alanyl and 3-naphthylalanyl residues;

X is hydrogen, alkyl, cycloalkyl, —$CH_2$-cyclohexyl or arylalkyl;

s, t and u are independently 0 or 1; and

K is hydroxy, alkoxy, phenoxy, benzyloxy or an amino moiety of the formula $R^5$—N—$R^6$ wherein:

$R^5$ is hydrogen; hydroxy; $C_{1-7}$ alkoxy; benzyloxy; phenyloxy; fluorine-substituted or unsubstituted $C_{1-7}$-linear or branched alkyl; $C_{1-12}$ linear or branched hydroxyalkyl; $C_{3-10}$-cycloalkyl; unsubstituted benzyl or mono-, di- or tri substituted benzyl, wherein the substituents are independently selected from the group consisting of: $CF_3$, nitro, $C_{1-7}$ alkylsulfonyl, $C_{1-4}$ alkoxy, phenoxy, benzoxy, halogen, $C_{1-4}$-alkyl, cyano, hydroxy, $N(CH_3)_2$, COOMe, COOEt, COOiPr, and $COONH_2$;

$R^6$ is hydrogen; fluorine-substituted or unsubstituted $C_{1-12}$ linear or branched alkyl; $C_{1-12}$ linear or branched hydroxyalkyl; $C_{3-10}$-cycloalkyl; —$(CH_2)_v$—$C_{3-7}$-cycloalkyl (v=0,1,2, or 3); norephedryl; norpseudoephedryl; quinolyl; pyrazyl; —$CH_2$-benzimidazolyl; (1)-adamantyl; (2)-adamantyl; —$CH_2$-adamantyl; alpha-methyl-benzyl; alpha-dimethylbenzyl; —$(CH_2)_v$-phenyl (v=0,1,2, or 3) wherein the phenyl group is unsubstituted or mono- or di-substituted and the substituents are independently selected from the group consisting of: $CF_3$, nitro, $C_{1-7}$ alkylsulfonyl, $C_{1-4}$ alkoxy, phenoxy, benzoxy, halogen, $C_{1-4}$-alkyl or fused alkyl, cyano, hydroxy, $N(CH_3)_2$, COOMe, COOEt, COOiPr, and $COONH_2$; —$(CH_2)_m$-naphthyl (m=0 or 1); —$(CH_2)_w$-benzhydryl (w=0,1, or 2); biphenyl; picolyl; benzothiazolyl; benzoisothiazolyl; benzopyrazolyl; benzoxazylyl; —$(CH_2)_m$-fluorenyl (m=0 or 1); pyrimidyl; —$(CH_2)_m$-indanyl (m=0 or 1); —$(CH_2CH_2O)_y$—$CH_3$ (y=0,1,2,3,4, or 5); —$(CH_2CH_2O)_y$—$CH_2CH_3$ (y=0,1,2,3,4, or 5); NH-phenyl wherein the phenyl group is unsubstituted or mono- or di-substituted and the substituents are independently selected from the group consisting of: $CF_3$, nitro, $C_{1-7}$ alkylsulfonyl, $C_{1-4}$ alkoxy, halogen, $C_{1-4}$ alkyl or fused alkyl, cyano, hydroxy, COOMe, COOEt, COOiPr, and $COONH_2$; —$NCH_3$—$C_6H_5$; —NH—$CH_2$—$C_6H_5$; —$NCH_3$—$CH_2$—$C_6H_5$; 5-membered unsubstituted or mono- or di-substituted heteroaryl wherein the substituents are selected from the group consisting of: $CF_3$, nitro, thiomethyl, thioethyl, $C_{3-6}$-cycloalkyl, —$CH_2$—COOEt, and $C_{3-4}$-alkylene group forming a bicyclic system with the heterocycle; phenyl; —$CHR^7$-5-membered heteroaryl wherein the heteroaryl group is unsubstituted or mono- or di-substituted wherein the substituents are independently selected from the group consisting of: $CF_3$, nitro, cyano, halogen, COOMe, COOEt, COOiPr, $CONH_2$, $C_{1-4}$-alkyl, $C_{1-4}$-alkoxy, phenyl, benzyl, naphthyl, and $C_{1-7}$-alkylsulfonyl; and $R^7$ is hydrogen, linear or branched $C_{1-5}$ alkyl, benzyl, or $R^7$ and $R^5$ together form a group —$(CH_2)_3$— or —$(CH_2)_4$— and the salts thereof with physiologically tolerated acids.

2. A method of claim 1 wherein said mammal is human.

3. A method of claim 1 wherein for the compound of Formula I $R^1$ and $R^2$ are each methyl or ethyl; X is isopropyl, sec-butyl or tert-butyl; s is 1; t and u are each 0; A is valyl, 2-ethylglycyl, isoleucyl or 2-tert-butylglycyl; B is N-methylvalyl, -2-ethylglycyl, -isoleucyl or -2-tertbutylglycyl; D is prolyl, 4-fluoroprolyl, thiazolidinyl-4-carbonyl, or 3,4-dehydroprolyl; E is prolyl, 4-fluoroprolyl, thiazolidinyl-4-carbonyl, homoprolyl, 3,4-dehydroprolyl or hydroxyprolyl; $R^5$ is hydrogen or $C_1$–$C_4$ alkoxy; and $R^6$ is a $C_1$–$C_{12}$ linear or branched alkyl group selected from the group of monovalent radicals consisting of:

—$C(CH_3)_3$;

—C—$CH_2$—$CH_3$; $(CH_3)_2$

—$C(CH_2$—$CH_3)_2$; $CH_3$

—CH—$C(CH_3)_3$, $CH_3$

—CH—$CH(CH_3)_2$; $C_2H_5$

—CH—$CH(CH_3)_2$; $CH(CH_3)_2$

—$C(CH_3)_2$—$CH(CH_3)_2$;

—$CH(CH_3)_2$;

—$CH(CH_3)CH_2CH_3$; and

—$CH(CH_3)CH(CH_3)_2$.

4. A method of claim 3 wherein said monovalent radical is —$C(CH_3)_3$.

5. A method of claim 1 wherein for the compound of Formula I $R^1$ and $R^2$ are each methyl or ethyl; X is isopropyl, sec-butyl or tert-butyl; s is 1; t and u are each 0; A is valyl, 2-ethylglycyl, isoleucyl or -2-tert-butylglycyl; B is N-methylvalyl, -2-ethylglycyl, -1-isoleucyl or -2-tertbutylglycyl; D is prolyl, 4-fluoroprolyl, thiazolidinyl-4-carbonyl, or 3,4-dehydroprolyl; E is prolyl, 4-fluoroprolyl, thiazolidinyl-4-carbonyl, homoprolyl, 3,4-dehydroprolyl or hydroxyprolyl; $R^5$ is hydrogen or $C_1$–$C_4$ alkoxy; and $R^6$ is selected from the group of monovalent radicals consisting of: $(CH_2)$v-phenyl (wherein v is 1), and α,α-dimethylbenzyl.

6. A method of claim 1 wherein for the compound of Formula I $R^1$ and $R^2$ are each methyl or ethyl; X is isopropyl, sec-butyl or tert-butyl; s is 1; t and u are each 0; A is valyl, 2-ethylglycyl, isoleucyl or 2-tert-butylglycyl; B is N-methylvalyl, -2-ethylglycyl -1-isoleucyl or -2-tertbutylglycyl; D is prolyl, 4-fluoroprolyl, thiazolidinyl-4-carbonyl, or 3,4-dehydroprolyl; E is prolyl, 4-fluoroprolyl, thiazolidinyl-4-carbonyl, homoprolyl, 3,4-dehydroprolyl or hydroxyprolyl; $R^5$ is hydrogen or $C_1$–$C_4$ alkoxy; and $R^6$ is a $C_1$–$C_{12}$ linear or branched hydroxyalkyl.

7. A method of claim 6 wherein $R^6$ is 3-hydroxy-1,1-dimethylpropyl.

8. A method of claim 1 wherein for the compound of Formula I $R^1$ and $R^2$ are each methyl or ethyl; X is isopropyl, sec-butyl or tert-butyl; s is 1; t and u are each 0; A is valyl, 2-ethylglycyl, isoleucyl or 2-tert-butylglycyl; B is N-methylvalyl, -2-ethylglycyl -isoleucyl or -2-tertbutylglycyl; D is prolyl, 4-fluoroprolyl, thiazolidinyl-4-carbonyl or 3,4-dehydroprolyl; E is prolyl, 4-fluoroprolyl thiazolidinyl-4-carbonyl, homoprolyl 3,4-dehydroxyprolyl or hydroxyprolyl; $R^5$ is hydrogen or $C_1$–$C_4$ alkoxy; and $R^6$ is a $C_{3-10}$ cycloalkyl selected from the group consisting of: (1)-adamantyl, (2)-adamantyl, cyclobutyl, cyclopentyl, cyclohexyl, 1-methylcyclopentyl, 1-methylcyclohexyl and octa-1-yl.

9. A method of claim 3 wherein for the compound of Formula I $R^1$ and $R^2$ are each methyl; X is isopropyl; s is 1; t and u are each 0; A is valyl; B is N-methylvalyl; D is prolyl; E is prolyl; $R^5$ is hydrogen and $R^6$ is tert-butyl.

10. A method of claim 1 wherein for the compound of Formula I $R^1$ and $R^2$ are each methyl; X is isopropyl; s is 1; t and u are each 0; A is valyl; B is N-methylvalyl; D is prolyl; E is prolyl; $R^5$ is benzyl and $R^6$ is hydrogen.

11. A method for the treatment of rheumatoid arthritis in a mammal, comprising administering to said mammal a pharmaceutical composition comprising:

a) a therapeutically effective amount of a compound of Formula I:

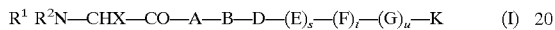

$$R^1\ R^2N\text{—}CHX\text{—}CO\text{—}A\text{—}B\text{—}D\text{—}(E)_s\text{—}(F)_t\text{—}(G)_u\text{—}K \qquad (I)$$

wherein:
$R^1$ is alkyl, cycloalkyl, alkylsulfonyl, fluoroalkyl, or aminosulfonyl;
$R^2$ is hydrogen, alkyl, fluoroalkyl or cycloalkyl;
$R^1$—N—$R^2$ together may be a pyrrolidino or piperidino residue;
A is a valyl, isoleucyl, leucyl, allo-isoleucyl, 2,2-dimethylglycyl, 2-cyclopropylglycyl, 2-cyclopentylglycyl, 3-tert-butylalanyl, 2-tert-butylglycyl, 3-cyclohexylalanyl, 2-ethylglycyl, 2-cyclohexylglycyl, norleucyl or norvalyl residue;
B is a N-alkyl-valyl, -norvalyl, -leucyl, -isoleucyl, -2-tert-butylglycyl, -3-tert-butylalanyl, -2-ethylglycyl, -2-cyclopropylglycyl, -2-cyclopentylglycyl, -norleucyl or -2-cyclohexylglycyl residue;
D is a prolyl, homoprolyl, hydroxyprolyl, 3,4-dehydroprolyl, 4-fluoroprolyl, 3-methylprolyl, 4-methylprolyl, 5-methylprolyl, azetidine-2-carbonyl, 3,3-dimethylprolyl, 4,4-difluoroprolyl, oxazolidine-4-carbonyl or thiazolidine-4-carbonyl residue;
E is a prolyl, homoprolyl, hydroxyprolyl, 3,4-dehydroprolyl, 4-fluoroprolyl, 3-methylprolyl, 4-methyl prolyl, 5-methylprolyl, azetidine-2-carbonyl, 3,3-dimethylprolyl, 4,4-difluoroprolyl, oxazolidine-4-carbonyl or thiazolidine-4-carbonyl residue;
F and G are independently selected from the group consisting of prolyl, homoprolyl, hydroxyprolyl, thiazolidinyl-4-carbonyl, 1-aminopentyl-1-carbonyl, valyl, 2-tert-butylglycyl, isoleucyl, leucyl, 3-cyclohexylalanyl, phenylalanyl, N-methylphenylalanyl, tetrahydrosioquinolyl-2-histidyl, 1-aminoindyl-1-carbonyl, 3-pyridylalanyl, 2-cyclohexylglycyl, norleucyl, norvalyl, neopentylglycyl, trytophanyl glycyl, 2,2-dimethylglycyl, alanyl, β-alanyl and 3-naphthylalanyl residues;
X is hydrogen, alkyl, cycloalkyl, —$CH_2$-cyclohexyl or arylalkyl;
s, t and u are independently 0 or 1; and
K is hydroxy, alkoxy, phenoxy, benzyloxy or an amino moiety of the formula $R^5$—N—$R^6$ wherein:

$R^5$ is hydrogen; hydroxy; $C_{1-7}$ alkoxy; benzyloxy; phenyloxy; fluorine-substituted or unsubstituted $C_{1-7}$-linear or branched alkyl; $C_{1-12}$ linear or branched hydroxyalkyl; $C_{3-10}$-cycloalkyl; unsubstituted benzyl or mono-, di- or tri substituted benzyl, wherein the substituents are independently selected from the group consisting of: $CF_3$, nitro, $C_{1-7}$ alkylsulfonyl, $C_{1-4}$ alkoxy, phenoxy, benzoxy, halogen, $C_{1-4}$-alkyl, cyano, hydroxy, $N(CH_3)_2$, COOMe, COOEt, COOiPr, and $COONH_2$;
$R^6$ is hydrogen; fluorine-substituted or unsubstituted $C_{1-12}$ linear or branched alkyl; $C_{1-12}$ linear or branched hydroxyalkyl; $C_{3-10}$-cycloalkyl; —$(CH_2)_v$—$C_{3-7}$-cycloalkyl (v=0,1,2 or 3); norephedryl; norpseudoephedryl; quinolyl; pyrazyl; —$CH_2$-benzimidazolyl; (1)-adamantyl; (2)-adamantyl; —$CH_2$-adamantyl; alpha-methyl-benzyl; alpha-dimethylbenzyl; —$(CH_2)_v$-phenyl (v=0,1,2, or 3) wherein the phenyl group is unsubstituted or mono- or di-substituted and the substituents are independently selected from the group consisting of: $CF_3$, nitro, $C_{1-7}$ alkylsulfonyl, $C_{1-4}$ alkoxy, phenoxy, benzoxy, halogen, $C_{1-4}$-alkyl or fused alkyl, cyano, hydroxy, $N(CH_3)_2$, COOMe, COOEt, COOiPr, and $COONH_2$; —$(CH_2)_m$-naphthyl (m=0 or 1); —$(CH_2)_w$-benzhydryl (w=0,1 or 2); biphenyl; picolyl; benzothiazolyl; benzoisothiazolyl; benzopyrazolyl; benzoxazolyl; —$(CH_2)_m$-fluorenyl (m=0 or 1); pyrimidyl; —$(CH_2)$m-indanyl (m=0 or 1); —$(CH_2CH_2O)_y$—$CH_3$ (y=0,1,2,3,4 or 5); —$(CH_2CH_2O)_y$—$CH_2CH_3$(y=0,1,2,3,4. or 5); NH-phenyl wherein the phenyl group is unsubstituted or mono- or di-substituted and the substituents are independently selected from the group consisting of: $CF_3$, nitro, $C_{1-7}$ alkylsulfonyl, $C_{1-4}$ alkoxy, halogen, $C_{1-4}$ alkyl or fused alkyl, cyano, hydroxy, COOMe, COOEt, COOiPr, and $COONH_2$; —$NCH_3$—$C_6H_5$; —NH—$CH_2$—$C_6H_5$; —$NCH_3$—$CH_2$—$C_6H_5$; 5-membered unsubstituted or mono- or di-substituted heteroaryl wherein the substituents are selected from the group consisting of: $CF_3$, nitro, thiomethyl, thioethyl, $C_{3-6}$-cycloalkyl, —$CH_2$—COOEt, and $C_{3-4}$-alkylene group forming a bicyclic system with the heterocycle; phenyl; —$CHR^7$-5-membered heteroaryl wherein the heteroaryl group is unsubstituted or mono- or di-substituted wherein the substituents are independently selected from the group consisting of: $CF_3$, nitro, cyano, halogen, COOMe, COOEt, COOiPr, $CONH_2$, $C_{1-4}$-alkyl $C_{1-4}$-alkoxy, phenyl, benzyl, naphthyl, and $C_{1-7}$-alkylsulfonyl; and $R^7$ is hydrogen, linear or branched $C_{1-5}$ alkyl, benzyl, or $R^7$ and $R^5$ together form a group —$(CH_2)_3$— or —$(CH_2)_4$— and the salts thereof with physiologically tolerated acids; and b) a therapeutically effective amount of a second antiarthritic drug selected from the group consisting of: a nonsteroidal antiinflammatory agent, an organic gold derivative, D-penicillamine, a 4-aminoquinoline, azathioprine, methotrexate, cyclosporin, an angiogenesis inhibitor, a monoclonal antibody to T cells, a monoclonal antibody to an adhesion molecule, a monoclonal antibody to a cytokine or growth factor, TNFR-IgG, IL-1 receptor antagonists and ICE inhibitors.

* * * * *